US010708553B2

(12) United States Patent
Sonoda et al.

(10) Patent No.: US 10,708,553 B2
(45) Date of Patent: Jul. 7, 2020

(54) MEASUREMENT SUPPORT DEVICE, ENDOSCOPE SYSTEM, PROCESSOR FOR ENDOSCOPE SYSTEM

(71) Applicant: FUJIFILM Corporation, Tokyo (JP)

(72) Inventors: Shinichiro Sonoda, Kanagawa (JP); Takeichi Tatsuta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/445,216

(22) Filed: Jun. 19, 2019

(65) Prior Publication Data

US 2019/0306467 A1    Oct. 3, 2019

Related U.S. Application Data

(63) Continuation of application No. PCT/JP2018/005058, filed on Feb. 14, 2018.

(30) Foreign Application Priority Data

Mar. 3, 2017  (JP) .................................. 2017-040618

(51) Int. Cl.
*H04N 7/18* (2006.01)
*A61B 1/00* (2006.01)
(Continued)

(52) U.S. Cl.
CPC ............... *H04N 7/183* (2013.01); *A61B 1/00* (2013.01); *A61B 1/0002* (2013.01);
(Continued)

(58) Field of Classification Search
CPC ......... H04N 2005/2255; H04N 13/204; H04N 7/183; H04N 7/18; A61B 1/0005;
(Continued)

(56) References Cited

U.S. PATENT DOCUMENTS 3,817,635 A    6/1974  Kawahara
4,935,810 A    6/1990  Nonami et al.
(Continued)

FOREIGN PATENT DOCUMENTS

GB    1233604       5/1971
JP    H02216404     8/1990
(Continued)

OTHER PUBLICATIONS

"International Search Report (Form PCT/ISA/210) of PCT/JP2018/005058," dated Mar. 27, 2018, with English translation thereof, pp. 1-5.
(Continued)

*Primary Examiner* — Sherrie Hsia
(74) *Attorney, Agent, or Firm* — JCIPRNET

(57) ABSTRACT

The invention aims at providing a measurement support device, an endoscope system, and a processor for an endoscope system capable of displaying an accurate indicator with a simple configuration. In a measurement support device related to one aspect of the invention, the coordinates of a spot, and coordinates of points indicating an actual size of a measurement target in a subject and indicating a circular marker distorted in accordance with distortion aberration of an imaging optical system are stored in association with each other in a storage unit, the coordinates of the points indicating the circular marker are acquired with reference to the storage unit on the basis of the measured coordinates of the spot, and the circular marker is displayed on the basis of the acquired coordinates. Thus, the distance measurement is unnecessary, the configuration is simple, and the processing load is low. Additionally, since the circular marker is displayed in the vicinity of the spot (for example, centering on a spot position), there is little deviation between the spot position and a marker position, the circular marker is accu- (Continued)

rate as an indicator. Additionally, since the indicator is not widely displayed, there is little processing load.

14 Claims, 22 Drawing Sheets

(51) Int. Cl.
*A61B 1/005* (2006.01)
*A61B 1/04* (2006.01)
*A61B 1/06* (2006.01)
*A61B 5/107* (2006.01)
*G06T 3/00* (2006.01)
*G06T 7/00* (2017.01)
*G02B 23/24* (2006.01)
*A61B 1/07* (2006.01)

(52) U.S. Cl.
CPC ............ *A61B 1/0005* (2013.01); *A61B 1/005* (2013.01); *A61B 1/00006* (2013.01); *A61B 1/00078* (2013.01); *A61B 1/04* (2013.01); *A61B 1/063* (2013.01); *A61B 1/0623* (2013.01); *A61B 1/0638* (2013.01); *A61B 1/0669* (2013.01); *A61B 5/1076* (2013.01); *A61B 5/1079* (2013.01); *G02B 23/24* (2013.01); *G06T 3/0006* (2013.01); *G06T 7/00* (2013.01); *A61B 1/07* (2013.01)

(58) Field of Classification Search
CPC ... A61B 1/00006; A61B 1/0002; A61B 1/005; A61B 1/00; A61B 1/00078; A61B 1/04; A61B 1/0623; A61B 1/063; A61B 1/0638; A61B 1/0669; A61B 1/07; A61B 5/1076; A61B 5/1079; G02B 23/24; G06T 3/0006; G06T 7/00
USPC ................ 348/65–68, 45, 74, 77; 356/241.1, 356/241.3–241.5; 385/117; 600/101, 600/103, 108, 109, 111, 112, 117, 160, 600/161, 164, 166, 178
See application file for complete search history.

(56) References Cited

U.S. PATENT DOCUMENTS

| | | | |
|---|---|---|---|
| 8,724,015 | B2 | 5/2014 | Yoshino |
| 2010/0272318 | A1 | 10/2010 | Cabiri et al. |
| 2011/0074950 | A1 | 3/2011 | Oka et al. |
| 2014/0036050 | A1 | 2/2014 | Yoshino |
| 2016/0217591 | A1 | 7/2016 | Krupnik |
| 2017/0105613 | A1 | 4/2017 | Tsuruta et al. |
| 2019/0069766 | A1* | 3/2019 | Mizukura ............ A61B 1/0623 |

FOREIGN PATENT DOCUMENTS

| | | |
|---|---|---|
| JP | H03231622 | 10/1991 |
| JP | H0473763 | 11/1992 |
| JP | H04323505 | 11/1992 |
| JP | H07136101 | 5/1995 |
| JP | 2002336188 | 11/2002 |
| JP | 2008122759 | 5/2008 |
| JP | 2011015721 | 1/2011 |
| JP | 2011069965 | 4/2011 |
| JP | 2012039255 | 2/2012 |
| JP | 2012222658 | 11/2012 |
| WO | 2016047191 | 3/2016 |

OTHER PUBLICATIONS

"Written Opinion of the International Searching Authority (Form PCT/ISA/237) of PCT/JP2018/005058," dated Mar. 27, 2018, with English translation thereof, pp. 1-7.
"Search Report of Europe Counterpart Application", dated Mar. 9, 2020, p. 1-p. 7.
"Office Action of Japan Counterpart Application", dated Mar. 19, 2020, with English translation thereof, pp. 1-6.

* cited by examiner

FIG. 14

| SPOT | COORDINATES OF POINTS INDICATING MARKER | | | | | |
|---|---|---|---|---|---|---|
| | FIRST | SECOND | ... | j-TH | ... | L-TH |
| P1 (X1, Y1) | P11 (X1 + ΔX11, Y1 + ΔY11) | P12 (X1 + ΔX12, Y1 + ΔY12) | ... | P1j (X1 + ΔX1j, Y1 + ΔY1j) | ... | P1L (X1 + ΔX1L, Y1 + ΔY1L) |
| P2 (X2, Y2) | P21 (X2 + ΔX21, Y2 + ΔY21) | P22 (X2 + ΔX22, Y2 + ΔY22) | ... | P2j (X2 + ΔX2j, Y2 + ΔY2j) | ... | P2L (X2 + ΔX2L, Y2 + ΔY2L) |
| P3 (X3, Y3) | P31 (X3 + ΔX31, Y3 + ΔY31) | P32 (X3 + ΔX32, Y3 + ΔY32) | ... | P3j (X3 + ΔX3j, Y3 + ΔY3j) | ... | P3L (X3 + ΔX3L, Y3 + ΔY3L) |
| ... | ... | ... | ... | ... | ... | ... |
| Pi (Xi, Yi) | Pi1 (Xi + ΔXi1, Yi + ΔYi1) | Pi2 (Xi + ΔXi2, Yi + ΔYi2) | ... | Pij (Xi + ΔXij, Yi + ΔYij) | ... | PiL (Xi + ΔXiL, Yi + ΔYiL) |
| ... | ... | ... | ... | ... | ... | ... |
| PK (XK, YK) | PK1 (XK + ΔXK1, YK + ΔYK1) | PK2 (XK + ΔXK2, YK + ΔYK2) | ... | PKj (XK + ΔXKj, YK + ΔYKj) | ... | PKL (XK + ΔXKL, YK + ΔYKL) |

MEASUREMENT SUPPORT DEVICE, ENDOSCOPE SYSTEM, PROCESSOR FOR ENDOSCOPE SYSTEM

CROSS-REFERENCE TO RELATED APPLICATIONS

The present application is a Continuation of PCT International Application No. PCT/JP2018/005058 filed on Feb. 14, 2018 claiming priority under 35 U.S.C § 119(a) to Japanese Patent Application No. 2017-040618 filed on Mar. 3, 2017. Each of the above applications is hereby expressly incorporated by reference, in their entirety, into the present application.

BACKGROUND OF THE INVENTION

1. Field of the Invention

The present invention relates to a measurement support device, an endoscope system, and a processor for an endoscope system, and particularly, to a measurement support device, an endoscope system, and a processor for an endoscope system that measures the size of a subject using measurement auxiliary light.

2. Description of the Related Art

In the field of measurement devices, such endoscopes, measuring the distance to a subject or calculating the length and the size of the subject is performed. For example, JP2008-122759A discloses that a subject distance is measured by a stereoscopic camera, and the size of a mark serving as a rough standard of the size of a subject is calculated on the basis of the subject distance and the angle of view of an endoscope, and the mark is displayed together with an image of the subject, and the size of the subject can be known from this mark.

Additionally, JP1995-136101A (JP-H07-136101A) discloses a technique of obtaining the distance to an observed part (observation target) and the size of the observed part, using measurement light. In JP1995-136101A (JP-H07-136101A), resolving power in the distance from a distal end of an endoscope insertion part to the observed part and the position of the observed part is improved by radiating the measurement light obliquely with respect to a radiation direction of the illumination light. Additionally, JP1995-136101A (JP-H07-136101A) discloses that a ruler image (scale image) of a ruler is displayed to overlap an acquired image and is used for measurement.

Additionally, JP2011-069965A discloses that aberration equal to the distortion aberration of an optical system is given to graduations serving as a measurement indicator, and distorted gradations are displayed in a synthesized manner on the captured image in real time. It is disclosed that the distortion of the graduations can be calculated by obtaining parameters and matrices for distortion correction by the Zhang's technique and the like and obtaining parameters and matrices for performing inverse transformation therefor.

SUMMARY OF THE INVENTION

In the above-described JP2008-122759A, two cameras are needed in order to measure the distance with the stereoscopic camera, and a distal end part of endoscope increases. Thus, a burden to the subject is high. Moreover, since the distance measurement is performed and the size of the mark is calculated on the basis of the result, system configuration and processing is complicated.

In the case of endoscopic observation, the subject often has irregularities. In this case, the imaging optical system does not confront the subject. For this reason, the measurement indicator is most likely to be an indicator of a size at a position where a spot of the measurement light hits, and is inaccurate as an indicator as the indicator goes away from the position of the spot. Therefore, in a case where the ruler image is moved and rotated at any positions and angles as in JP1995-136101A (JP-H07-136101A), the measurement indicator is likely to be inaccurate as an indicator.

Additionally, in JP2011-069965A, the quantity of received laser light is measured by a distance sensor, distance is calculated at an imaging frame rate, and graduation width in the distance is calculated. Thus, system configuration and processing become complicated. Additionally, in a case where the graduations are displayed in a wide range of a screen, it is necessary to correct distortion in a wide range. Therefore, the amount of calculation of transformation parameters and matrices increases, and the load is high. In addition, in the Zhang's technique, the entire screen is expressed by a set of (six) parameters. Therefore, the accuracy of correction is low. Moreover, in a case where the graduations are displayed in the wide range of the screen, in JP1995-136101A (JP-H07-136101A), a peripheral part of the graduations becomes far from the spot similarly to those described above. Therefore, the graduations are likely to be inaccurate as an indicator.

In this way, In the related art, the load resulting from the generation of the indicator is high, and it is difficult to displays an accurate indicator.

The invention has been made in view of such circumstances, and an object thereof is providing a measurement support device, an endoscope system, and a processor for an endoscope system capable of displaying an accurate indicator with a simple configuration.

In order to achieve the above-described object, a measurement support device related to a first aspect of the invention comprises a head that emits measurement auxiliary light; an imaging unit that captures an image of a subject on which a spot is formed with the measurement auxiliary light via an imaging optical system and an imaging element; a measurement unit that measures coordinates of the spot in the image; a storage unit that stores the coordinates of the spot and coordinates of points indicating an actual size of a measurement target in the subject and indicating a circular marker distorted in accordance with distortion aberration of the imaging optical system in association with each other and that stores the coordinates of the points indicating the circular marker with respect to a plurality of points in a trajectory along which the spot moves on the image in a case where an imaging distance of the image is changed; a coordinate acquisition unit that refers the storage unit on the basis of the measured coordinates of the spot and acquires the coordinates of the points indicating the circular marker corresponding to the coordinates of the spot; and a display control unit that causes the circular marker to be displayed in the vicinity of the spot in the image on the basis of the acquired coordinates. The head emits the measurement auxiliary light that has an inclination angle that is not 0 degrees with respect to an optical axis of the imaging optical system and crosses an angle of view of the imaging optical system, in a case where an optical axis of the measurement auxiliary light is projected on a plane including the optical axis of the imaging optical system.

According to the first aspect, the coordinates of the points indicating the circular marker (distorted circular marker) are acquired with reference to the storage unit on the basis of the coordinates of the spot, and the circular marker is displayed on the basis of the acquired coordinates. Thus, the distance measurement is unnecessary, the configuration is simple, and the processing load is low. Additionally, since the circular marker is displayed in the vicinity of the spot (for example, centering on a spot position), there is little deviation between the spot position and a marker position, the circular marker is accurate as an indicator. Additionally, since the indicator is not widely displayed, there is little processing load.

In the first aspect, in a case where the imaging distance has been changed, the trajectory along which the spot diameter moves on the image is uniquely determined in accordance with a relationship between the optical axis of the imaging optical system and the optical axis of the measurement auxiliary light. Thus, the coordinates of the marker can be obtained with respect a point on this trajectory. In addition, since the position of the spot in the trajectory corresponds to the imaging distance, display sizes of the marker in the image are different from each other even in a case where actual sizes are the same in a case where spot positions are different from each other.

Additionally, in the first aspect, as for the expression "the coordinates of the points indicating the circular marker with respect to a plurality of points in a trajectory are stored", data may be stored to many points (for example, all the pixels) on the trajectory or data may be stored only with respect to some points (pixels) on the trajectory. The expression "the coordinates of the points indicating the circular marker are acquired" includes an aspect in which stored coordinates stored are used as they are, and an aspect in which coordinates to be used for display are calculated on the basis of the stored coordinates.

Additionally, according to the first aspect, the optical axis of the measurement auxiliary light has the inclination angle, which is not 0 degrees with respect to the optical axis of the imaging optical system, and crosses the angle of view of the imaging optical system, in a case where the optical axis of the measurement auxiliary light is projected on the plane including the optical axis of the imaging optical system. Thus, by setting the inclination angle appropriately, the measurement auxiliary light can enter the visual field of the imaging optical system even in a case where the observation distance is short. Moreover, since the optical axis of the measurement auxiliary light has the inclination angle that is not 0 degrees with respect to the optical axis of the imaging optical system in a case where the optical axis of the measurement auxiliary light is projected on the plane including the optical axis of the imaging optical system, the sensitivity of a change in the position of the spot to a change in the observation distance is high, and measurement accuracy is high.

In this way, according to the measurement support device related to the first aspect, an accurate indicator can be displayed with a simple configuration. In addition, in the first aspect, the display of the marker may be performed in real time (single time for each frame which a spot image is acquired or for every plural frames), or may be performed off-line (in a case where an image on which a spot is formed is acquired, post marker display is possible).

In the measurement support device related to a second aspect based on the first aspect, the coordinate acquisition unit acquires the coordinates of the points indicating the circular marker corresponding to a point of which a distance from the spot is equal to or smaller than a threshold value, among the plurality of points. In a case where the coordinates of the points indicating the circular marker are acquired for a point away from the spot, an inaccurate marker (a marker that is different from a marker to be originally displayed in terms of shape and size) is obtained. Thus, an accurate marker can be displayed by acquiring the coordinates of the points indicating the circular marker corresponding to the point of which the distance from the spot is equal to or smaller than the threshold value, among the plurality of points in the trajectory as in the second aspect. The threshold value is determined such that the accurate marker can be displayed. In addition, in the second aspect, in a case where the coordinates of the points indicating the marker with respect to the position of the spot are stored, the above-described "distance" is zero.

In the measurement support device related to a third aspect based on the first aspect, the coordinate acquisition unit acquires the coordinates of the points indicating the circular marker by interpolating coordinates corresponding to two or more points sandwiching the spot, among the plurality of points. The third aspect is one aspect of the coordinate acquisition, and such processing can be performed in a case where the coordinates of the points indicating the marker for all the points (pixels) in the trajectory are not stored.

In the measurement support device related to a fourth aspect based on the first aspect, the coordinate acquisition unit acquires the coordinates of the points indicating the circular marker by interpolating coordinates corresponding to two or more points, which do not sandwich the spot, among the plurality of points. The fourth aspect is another aspect of the coordinate acquisition, and such processing can be performed in a case where the coordinates of the points indicating the marker for all the points (pixels) in the trajectory are not stored.

In the measurement support device related to a fifth aspect based on any one of the first to fourth aspects, the storage unit stores the coordinates of the points indicating the circular marker in correspondence with a range where size measurement of the measurement target by the circular marker is effective, in the image. Since the distortion aberration of the imaging optical system generally becomes large at a peripheral part of the angle of view, distortion of the subject becomes large at a peripheral part of the image, and measurement accuracy resulting from the marker degrades in many cases. Additionally, there is a case where a perfect marker cannot be displayed at the peripheral part of the image (for example, a portion of the marker protrudes from a screen). Thus, in the fifth aspect, such a problem does not occur, and the coordinates of the points indicating the circular marker are stored in correspondence with a range where the size measurement of the measurement target by the circular marker is effective. In addition, the expression "the range where the size measurement is effective" can be determined in consideration of the measurement accuracy.

In the measurement support device related to a sixth aspect based on any one of the first to fifth aspects, the storage unit stores coordinates of a plurality of first points, which are actually measured in correspondence with a circle centering on the spot, and coordinates of a plurality of second points generated by interpolating the plurality of first points as the coordinates of the points indicating the circular marker, and the coordinate acquisition unit acquire the coordinates of the plurality of first points and the coordinates of the plurality of second points as the coordinates of the points indicating the circular marker. The sixth aspect is one aspect of the coordinate acquisition, and the actually measured coordinates (the coordinates of the first points) and the coordinates (the coordinates of the second points) obtained by the interpolation are stored as the coordinates of the points indicating the marker. That is, the coordinates about may not be actually measured for all the points to be used for the marker display.

In the measurement support device related to a seventh aspect based the sixth aspect, the storage unit stores coordinates of points, which are obtained by linearly interpolating the plurality of first points in an angular direction and a radial direction of the circle, as the coordinates of the plurality of second points. The 7th aspect is one specific aspect of the "interpolation" in the sixth aspect.

In the measurement support device related to an eighth aspect based on any one of the first to fifth aspects, the storage unit stores a transformation matrix for projectively transform a distorted lattice region including the circular marker centering on the spot to a square lattice region, in the image, and the coordinate acquisition unit acquires the coordinates of the points indicating the circular marker in the square lattice region transformed by the transformation matrix, and acquires the coordinates of the points indicating the circular marker in the distorted lattice region by inversely transforming the acquired coordinates by an inverse matrix of the transformation matrix. Since the eighth aspect is still another aspect of the coordinate acquisition, and the coordinates of the points indicating the circular marker in the square lattice region can be accurately and easily acquired, the coordinates in the distorted lattice region can be accurately and easily calculated by inversely transforming the coordinates acquired in the square lattice region. A projective transformation matrix can be used as the transformation matrix. In addition, an inverse matrix of the transformation matrix may be stored, or may be obtained from the transformation matrix.

In the measurement support device related to a ninth aspect based on the eighth aspect, the storage unit stores the transformation matrix for each of a plurality of small regions obtained by dividing the distorted lattice region and the square lattice region into 2×m×n pieces in a case where m and n are positive integers, and the coordinate acquisition unit applies a same transformation matrix out of the plurality of transformation matrices and a same inverse matrix out of the plurality inverse matrices to pixels, which belong to a same small region, among pixels of the image. The amount of storage can be reduced by applying the same transformation matrix and inverse matrix for each small region as in the ninth aspect.

In the measurement support device related to a tenth aspect based on the ninth aspect, the storage unit stores the transformation matrices, using a plurality of regions, which include the distorted lattice region in a case where the imaging distance is a farthest end of a measurement distance range, and the distorted lattice region in a case where the imaging distance is a nearest end of the measurement distance range, and are obtained by dividing a partial region in the image, and which are divided to be smaller than a size of lattice cells of the distorted lattice region in the farthest end, as the plurality of small regions, and the coordinate acquisition unit acquires the coordinates of the points indicating the circular marker, using the transformation matrices stored for the plurality of small regions. In the tenth aspect, a partial region of the captured image is divided into the regions and the transformation matrices are stored. Thus, it is not necessary to store the transformation matrices with respect to the entire image, and the partial region is low.

Additionally, an accurate marker can be displayed by storing the transformation matrices with respect to the plurality of regions divided to be smaller than the size (the size of a lattice becomes the smallest since it is the farthest end) of a lattice cell at the farthest end of the distance range (measurement distance range) where the measurement by the circular marker is effective.

In the measurement support device related to an eleventh aspect based on any one of the eighth to tenth aspects, the transformation matrix is an affine transformation matrix. The eleventh aspect shows one aspect of the transformation matrix, and three points of the distorted image can be transformed to a square lattice image in one affine transformation matrix.

In order to achieve the above-described object, an endoscope system related to the invention of the invention comprises the measurement support device according to any one of the first to eleventh aspects. Since the endoscope system related to the twelfth aspect comprises the measurement support device related to any one of the first to eleventh aspect, an accurate indicator can be displayed with a simple configuration.

The endoscope system related to a twelfth aspect based on the thirteen aspect further comprising an endoscope having an insertion part to be inserted into a subject, the insertion part having a distal end hard part and a bending part connected to a proximal end side of the distal end hard part, and a flexible part connected to a proximal end side of the bending part, and an operating part connected to a proximal end side of the insertion part. The distal end hard part is provided with the head, and an imaging lens for forming an optical image of the spot on the imaging element. The thirteenth aspect defines one aspect of the configuration of the distal end hard part of the endoscope.

In order to achieve the above-described object, a processor for an endoscope system related to a fourteen aspect of the aspect, the processor comprising the processor for the endoscope system related to the twelfth or thirteen aspect, a measurement unit, a storage unit, a coordinate acquisition unit, and a display control unit. According to the fourteenth aspect, an accurate indicator can be displayed with a simple configuration similarly to the first aspect.

As described above according to the measurement support device, the endoscope system, and the processor for an endoscope system of the invention, an accurate indicator can be displayed with a simple configuration.

BRIEF DESCRIPTION OF THE DRAWINGS

FIG. 14 is a view illustrating a state where the spot positions and the coordinates of the points indicating the distorted circular marker are associated with each other and stored.

DESCRIPTION OF THE PREFERRED EMBODIMENTS

Hereinafter, embodiments of a measurement support device, an endoscope system, and a processor for an endoscope system related to the invention will be described in detail, referring to the accompanying drawings.

First Embodiment

Figure 1:
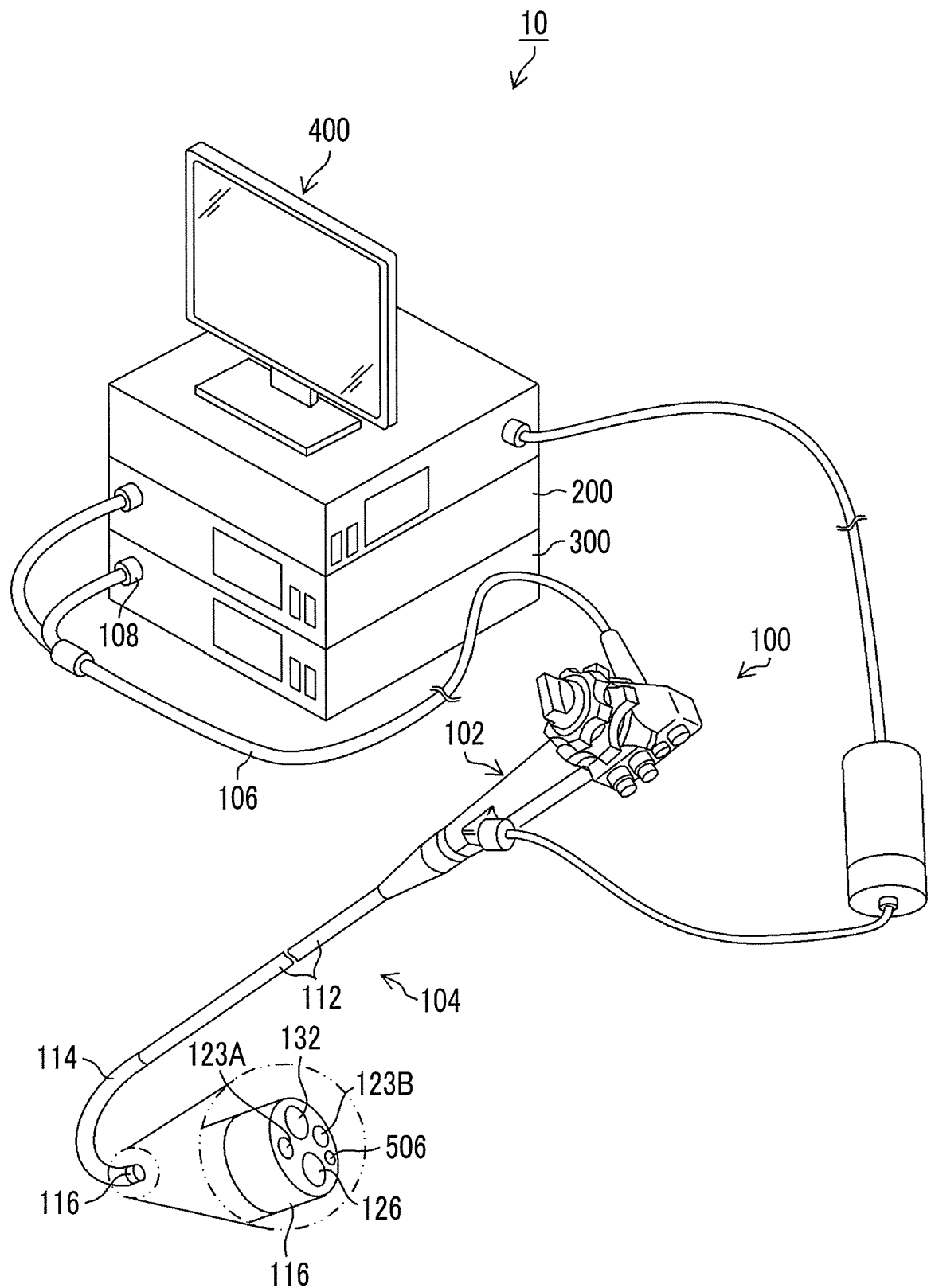
FIG. 1 is a view illustrating an entire configuration of an endoscope system related to a first embodiment of the invention.
Figure 2:
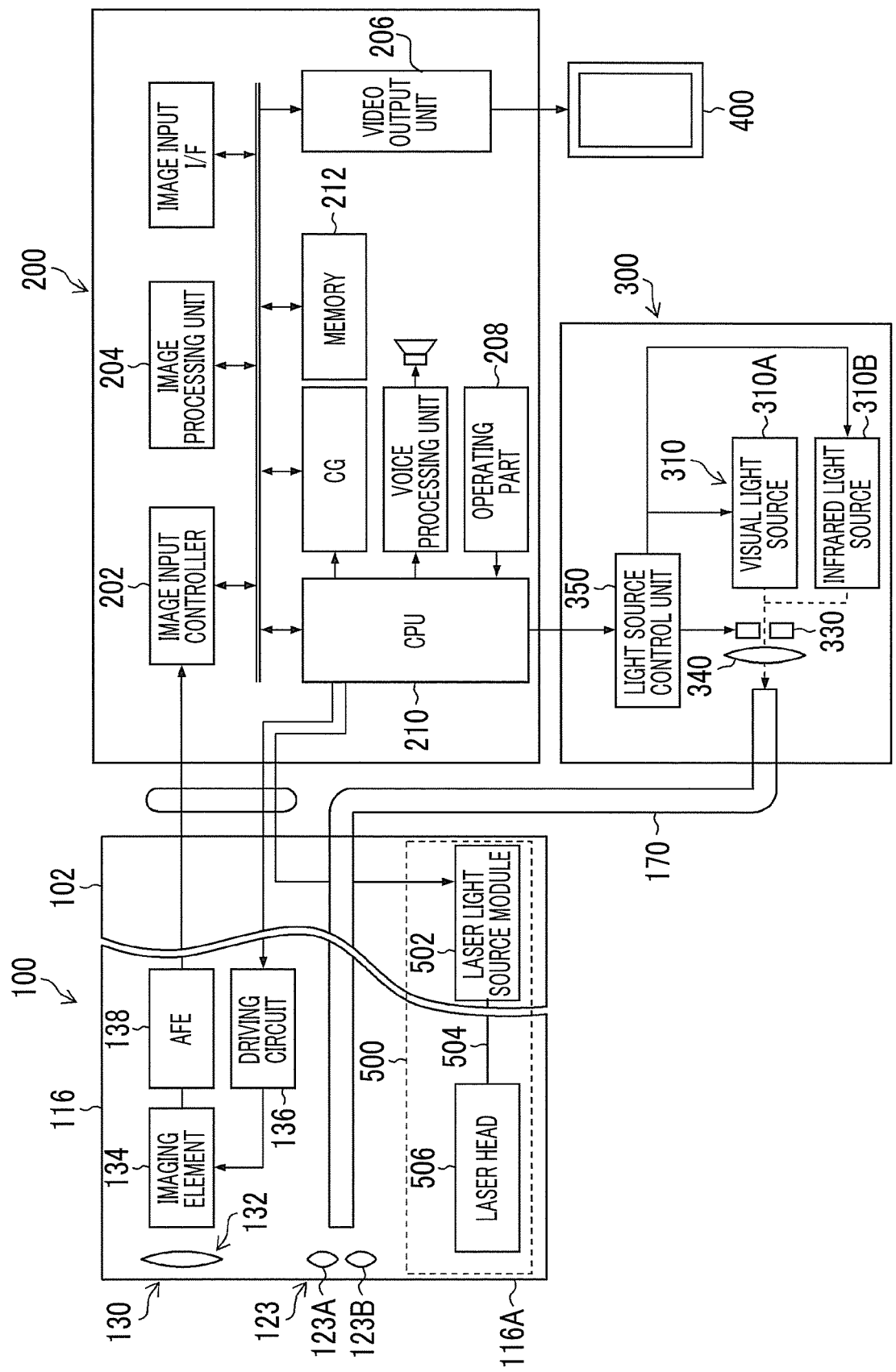
FIG. 2 is a block diagram illustrating the configuration of the endoscope system related to the first embodiment of the invention.

FIG. 1 is an external view illustrating an endoscope system 10 (a measurement support device, an endoscope system, and a processor for an endoscope system) related to a first embodiment, and FIG. 2 is a block diagram illustrating the configuration of main parts of the endoscope system 10. As illustrated in FIGS. 1 and 2, the endoscope system 10 comprises an endoscope body 100 (endoscope), a processor 200 (processor for an endoscope system), a light source device 300, and a monitor 400 (display device).

<Configuration of Endoscope Body>

The endoscope body 100 comprises a proximal operating part 102 (operating part), and an insertion part 104 (insertion part) provided continuously with at the proximal operating part 102. An operator grips the proximal operating part 102 to operate the endoscope body 100, and inserts the insertion part 104 into the body of a subject to observe the body. The insertion part 104 is constituted of a flexible part 112 (flexible part), a bending part 114 (bending part), and a distal end hard part 116 (distal end hard part) sequentially from the proximal operating part 102 side. By operating the proximal operating part 102, the bending part 114 can be bent to change the orientation of the distal end hard part 116 vertically and horizontally. The distal end hard part 116 is provided with an imaging optical system 130 (imaging unit), an illumination unit 123, a forceps port 126, and a laser module 500, and the like (refer to FIGS. 1 to 3).

During observation or treatment, visible light, infrared light, or both can be radiated from illumination lenses 123A and 123B of the illumination unit 123 by the operation of an operating part 208 (refer to FIG. 2). Additionally, washing water is released from a water supply nozzle (not illustrated) by the operation of the operating part 208, so that an imaging lens 132 (imaging lens) of the imaging optical system 130 and the illumination lenses 123A and 123B can be washed. A pipe line (not illustrated) communicates with the forceps port 126 that opens at the distal end hard part 116, and a treatment tool (not illustrated) for tumor removal or the like is inserted through to the pipe line is appropriately moved forward and backward so as to perform treatment required for the subject.

Figure 3:
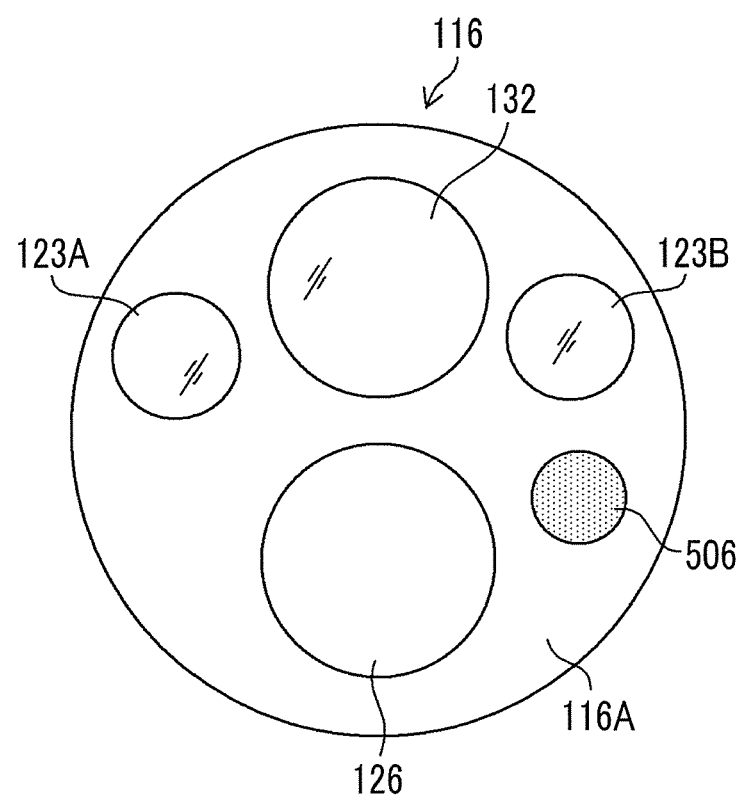
FIG. 3 is a view illustrating the configuration of a distal-end-side end surface of a distal end hard part.

As illustrated in FIGS. 1 to 3, the imaging lens 132 is disposed on a distal-end-side end surface 116A of the distal end hard part 116, and a complementary metal-oxide semiconductor (CMOS) type imaging element 134 (an imaging element or a color imaging element), a driving circuit 136, and an analog front end (AFE) 138 are disposed at the back of the imaging lens 132 so as to output image signals. The imaging element 134 is a color imaging element, and includes a plurality of pixels constituted of a plurality of light receiving elements arranged in a matrix (two-dimensional array) in a specific pattern arrangement (a Bayer arrangement, an X-Trans (registered trademark) arrangement, a honeycomb arrangement, or the like). Each pixel include a microlens, a red (R), green (G), or blue (B) color filter, and a photoelectric conversion part (photodiode or the like). The imaging optical system 130 may generate a color image from pixel signals of three colors of red, green, and blue, or may generate an image from pixel signals of any one color or two colors among red, green, and blue.

In addition, in the first embodiment, a case where the imaging element 134 is a CMOS type imaging element is described. However, the imaging element 134 may be of charge coupled device (CCD) type.

An image of the subject (a tumor region or an affected region) or an optical image of a spot (to be described below) is formed on a light-receiving surface (imaging surface) of the imaging element 134 by the imaging lens 132, is converted into electrical signals, is output to the endoscope processor 200 via a signal cable (not illustrated), and is converted into video signals. Accordingly, an observation image, a distorted circular marker, and the like are displayed on the monitor 400 connected to the processor 200.

Additionally, the illumination lenses 123A (for visible light) and 123B (for infrared light) of the illumination unit 123 are provided adjacent to the imaging lens 132 on the distal-end-side end surface 116A of the distal end hard part 116. An exit end of a light guide 170 to be described below is disposed at the back of the illumination lenses 123A and 123B, the light guide 170 is inserted through the insertion part 104, the proximal operating part 102, and an universal cable 106, and an incidence end of the light guide 170 is disposed within a light guide connector 108.

Figure 4:
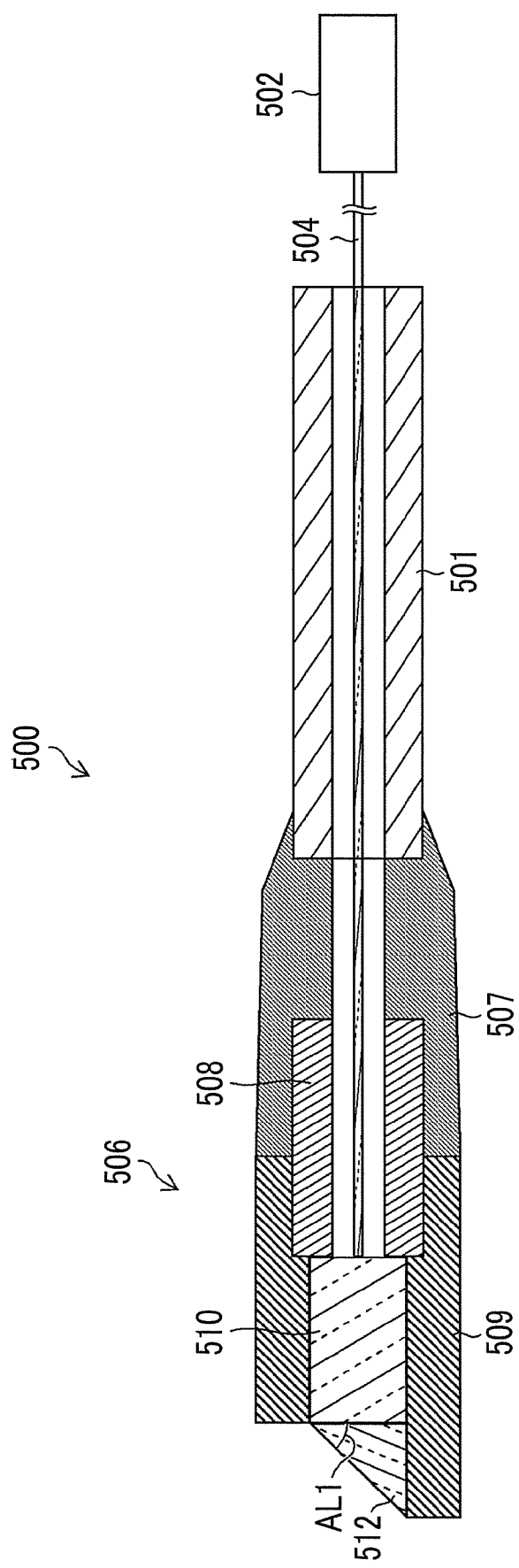
FIG. 4 is a view illustrating the configuration of a laser module.

The distal-end-side end surface 116A is further provided with a laser head 506 of the laser module 500 and is irradiated with spot light (measurement auxiliary light) via a prism 512 (refer to FIG. 4). The configuration of the laser module 500 will be described below. In addition, in the first embodiment, as illustrated in FIG. 3, the laser head 506 is provided separately from the forceps port 126. However, the laser head 506 may be removably inserted through the pipe line (not illustrated) that communicates with the forceps port 126 opening at the distal end hard part 116. Additionally, the laser head 506 may be provided between the imaging lens 132 and the forceps port 126.

<Configuration of Laser Module>

As illustrated in FIGS. 2 and 4, the laser module 500 comprises a laser light source module 502, an optical fiber 504, and a laser head 506 (head). A proximal end side (laser light source module 502 side) of the optical fiber 504 is covered with a fiber covering 501, a distal end side (a side from which laser light is emitted) thereof is inserted into a ferrule 508 (ferrule) and is bonded with an adhesive, and an end surface is ground. A graded index (GRIN) lens 510 is mounted on a distal end side of the ferrule 508, and a prism 512 is mounted on a distal end side of the GRIN lens 510 so as to form a joined body. The ferrule 508 is a member for holding and connecting the optical fiber 504, and a hole for allowing the optical fiber 504 to be inserted therethrough is made empty in an axial direction (leftward-rightward direction of FIG. 4) at a central part of the ferrule. A reinforcing member 507 is provided outside the ferrule 508 and the fiber covering 501 to protect an optical fiber 504 or the like. The ferrule 508, the GRIN lens 510, and the prism 512 are housed in a housing 509 and are integrated with the reinforcing member 507 and the fiber covering 501 to constitute the laser head 506.

In the laser head 506, for example, one having a diameter of 0.8 mm to 1.25 mm can be used as the ferrule 508. A fine-diameter ferrule is more preferable for downsizing. By virtue of the above-described configuration, the total diameter of the laser head 506 can be 1.0 mm to 1.5 mm.

The laser module 500 configured in this way is mounted on the insertion part 104. Specifically, as illustrated in FIG. 2, the laser light source module 502 is provided at the proximal operating part 102, the laser head 506 is provided at the distal end hard part 116, and the optical fiber 504 guides the laser light from the laser light source module 502 to the laser head 506. In addition, the laser light source module 502 may be provided within the light source device 300 so as to guide the laser light to the distal end hard part 116 with the optical fiber 504.

Figure 5:
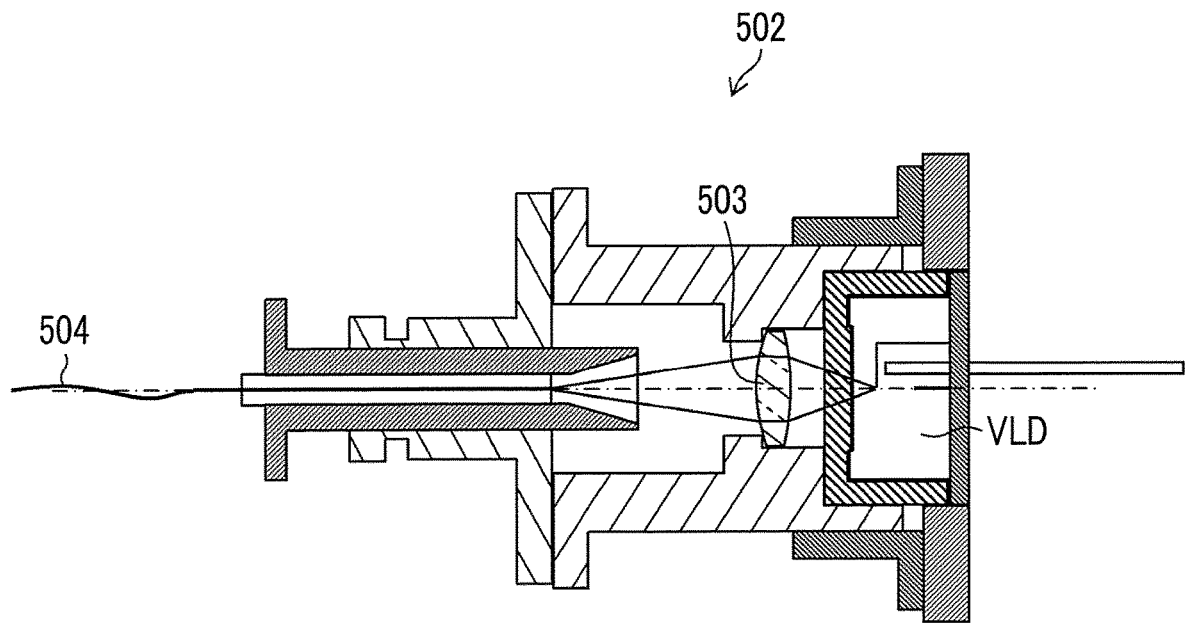
FIG. 5 is a cross-sectional view illustrating the configuration of a laser light source module.

As illustrated in FIG. 5, the laser light source module 502 is a pigtail type module (transmitter optical sub-assembly (TOSA)) comprising a visible laser diode (VLD) that has electrical power supplied thereto from a power source (not illustrated) and emits the laser light (measurement auxiliary light) of a visible wavelength range, and a condensing lens 503 that condenses the laser light emitted from the VLD. The laser light can be emitted as necessary by the control of the processor 200 (CPU 210). By emitting the laser light only in a case where measurement is performed (measurement mode), the laser light can be used similarly to a normal endoscope during non-emission (normal mode).

In the first embodiment, the laser light emitted by the VLD can be red laser light with a wavelength of 650 nm by a semiconductor laser. However, the wavelength of the laser light in the invention is not limited to this aspect. The laser light condensed by the condensing lens 503 is guided up to the GRIN lens 510 by the optical fiber 504. The optical fiber 504 is an optical fiber that propagates the laser light in a single transverse mode, and can form a spot with a small clear diameter, so that the size of the subject (measurement target) can be accurately measured. A relay connector may be provided in the middle of the optical fiber 504. In addition, in a case where the size of spot diameter or clearness does not pose a measurement problem depending on observation conditions, such as the type or size of the subject, an optical fiber that propagates the laser light in a multi-mode may be used as the optical fiber 504. Additionally, as the light source, a light-emitting diode (LED) may be used instead of the semiconductor laser, or the semiconductor laser may be used in an LED light emission state equal to or less than an oscillation threshold value.

The GRIN lens 510 is a cylindrical graded index type lens (radial type) of which the refractive index is highest on the optical axis and decrease radially outward, and functions as a collimator that makes the laser light, which is guided by the optical fiber 504 and enters, into a parallel beam and emits the parallel beam. The spread of the beam emitted from the GRIN lens 510 can be adjusted by adjusting the length of the GRIN lens 510, and about λ/4 pitch (λ is the wavelength of the laser light) or the like may be used to emit the laser light as the parallel beam.

The prism 512 is mounted on a distal end side of the GRIN lens 510. The prism 512 is an optical member for changing the emission direction of the measurement auxiliary light. By changing the emission direction, in a case where the optical axis of the measurement auxiliary light is projected on a plane including the optical axis of the imaging optical system, the optical axis of the measurement auxiliary light has an inclination angle, which is not 0 degrees with respect to the optical axis of the imaging optical system, and the measurement auxiliary light crosses the angle of view of the imaging optical system. The prism 512 is formed with a size near the lens diameter of the GRIN lens 510, and a distal end surface thereof is cut obliquely and has an apex angle AL1 according to the above-described inclination angle. The value of the apex angle AU can be set in accordance with the emission direction of the laser light and other conditions.

<Relationship Between Optical Axis of Imaging Optical System and Optical Axis of Measurement Auxiliary Light>

Figure 6:
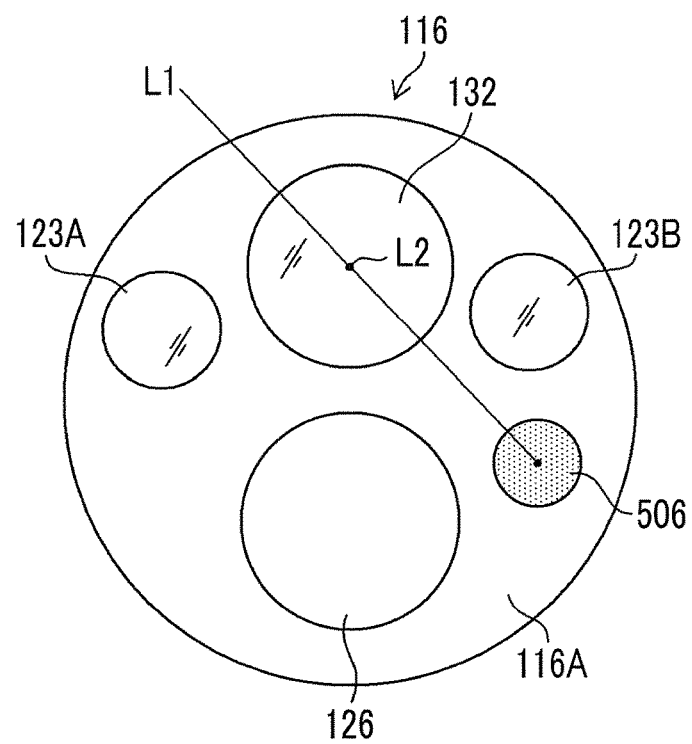
FIG. 6 is a view illustrating a relationship between an optical axis of an imaging optical system, and an optical axis of a measurement auxiliary light.

FIG. 6 is a view illustrating a state where the distal end hard part 116 related to the first embodiment is seen from the front (subject side), and is a view corresponding to the configuration of FIG. 3. In the first embodiment, an optical axis L1 of the measurement auxiliary light and an optical axis L2 of the imaging optical system are present on the same plane and intersect each other on the same plane. Hence, in a case where the distal end hard part 116 is seen from the front (subject side), as illustrated in FIG. 6, the optical axis L2 appears to pass on the optical axis L1.

In addition, the relationship between the optical axis L1 of the measurement auxiliary light and the optical axis L2 of the imaging optical system in the invention may not be limited to the above-described aspect in which "the optical axis of the measurement auxiliary light and the optical axis of the imaging optical system are present on the same plane and intersect each other on the same plane", and the optical axis of the measurement auxiliary light may not be present on the same plane as the optical axis of the imaging optical system. However, even in such a case, in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the angle of view of the imaging optical system.

In a case where the measurement using the measurement auxiliary light is performed, and in a case where the optical axis of the measurement auxiliary light is parallel to the optical axis of the imaging optical system (the inclination angle is 0 degrees), the distance up to a point where the optical axis of the measurement auxiliary light crosses the angle of view of the imaging optical system becomes long depending on the spacing between the optical axes. As a result, a spot cannot be imaged in an closest range, and the measurement becomes difficult. Additionally, in a case where the optical axis of the measurement auxiliary light is parallel to the optical axis of the imaging optical system, there is a case where the sensitivity of spot positions change with respect to a change in observation distance is low and sufficient measurement accuracy is not obtained. In contrast, according to the configuration in which, "in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the angle of view of the imaging optical system" as in the first embodiment, the measurement can be made at an observation distance of a wide range from the closest range to a long range. Additionally, since the sensitivity of the spot positions changes with respect to the distance change is high, the measurement can be made with high accuracy.

<Configuration of Light Source Device>

As illustrated in FIG. 2, the light source device 300 is constituted of a light source 310 for illumination, a stop 330, a condensing lens 340, a light source control unit 350, and the like, and makes illumination light (the visible light or infrared light) incident on the light guide 170. The light source 310 comprises a visible light source 310A, and an infrared light source 310B, and is capable of radiating both the visible light and the infrared light. The illuminance of the illumination light by the visible light source 310A and the infrared light source 310B is controlled by the light source control unit 350, and is capable of lowering the illuminance of the illumination light as necessary or stopping the illumination, in a case where a spot is imaged and measured (in the measurement mode).

By coupling the light guide connector 108 (refer to FIG. 1) to the light source device 300, the illumination light radiated from the light source device 300 is transmitted to the illumination lenses 123A and 123B via the light guide 170 and is radiated to an observation range from the illumination lenses 123A and 123B.

<Configuration of Processor>

Next, the configuration of the endoscope processor 200 (a measurement unit, a storage unit, a coordinate acquisition unit, and a display control unit) will be described with reference to FIG. 2. The endoscope processor 200 inputs the image signals output from the endoscope body 100 via an image input controller 202, and performs image processing required by an image processing unit 204 (the measurement unit, the coordinate acquisition unit, and the display control unit) to output the image signals via a video output unit 206. Accordingly, an observation image is displayed on the monitor 400 (display device). These kinds of processing are performed under the control of a central processing unit (CPU) 210. That is, the CPU 210 has functions as the measurement unit, the coordinate acquisition unit, and the display control unit. In the image processing unit 204, switching and overlap display of images displayed on the monitor 400, electronic zooming processing, display of images according to operation modes, extraction of a specific component (for example, a brightness signal) from the image signals, and the like are performed in addition to image processing, such as white balance adjustment. Additionally, in the image processing unit 204, measurement of spot positions on the imaging surface of the imaging element 134 and calculation of the size (the number of pixels) of a marker based on the measured positions are performed (will be described below). The hardware structure for executing various kinds of processing in the image processing unit 204 may include processors (electric circuits), such as a central processing unit (CPU), a field programmable gate array (FPGA), and an application specific integrated circuit (ASIC). The image processing unit 204 may be constituted of one processor, or may be constituted of a combination of a plurality of processors. The memory 212 (storage unit) includes a storage element for temporary storage during various processing and a nonvolatile storage element (a non-temporary recording medium), and coordinates of spots, and coordinates of points indicating the actual size of the measurement target in the subject and indicating the circular marker distorted in accordance with the distortion aberration of the imaging optical system 130 are stored in association with each other (will be described below) under the control of the CPU 210 and/or the image processing unit 204. Additionally, computer-readable codes of the program that makes the CPU 210 and/or the image processing unit 204 execute a measurement support method to be described below is stored in the memory 212.

Additionally, the endoscope processor 200 comprises the operating part 208. The operating part 208 comprises an operation mode setting switch, a water supply instruction button, and the like that are not illustrated, and can operate radiation of the visible light and/or the infrared light. Additionally, the operating part 208 includes devices, such as a keyboard and a mouse, which are not illustrated, and can input various processing conditions, display conditions, and the like via these devices.

<Observation by Endoscope>

Figure 7:
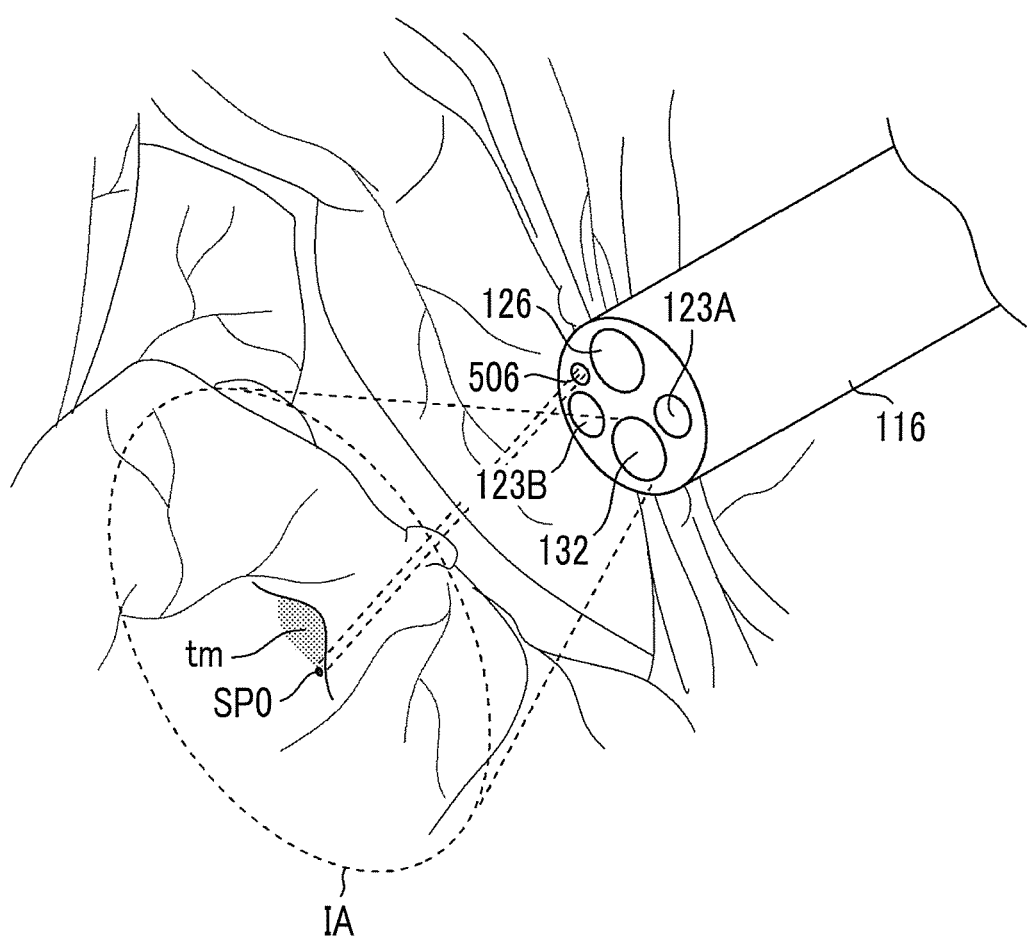
FIG. 7 is a view illustrating a state where an insertion part of the endoscope is inserted into a subject.

FIG. 7 is a view illustrating a state where the insertion part 104 of the endoscope body 100 is inserted into the subject, and illustrates a state where an observation image is acquired for an imaging range IA via the imaging optical system 130. FIG. 7 illustrates a state where a spot SP0 is formed in the vicinity of a tumor tm (a portion that bulges in black).

<Flow of Measurement Processing>

Figure 8:
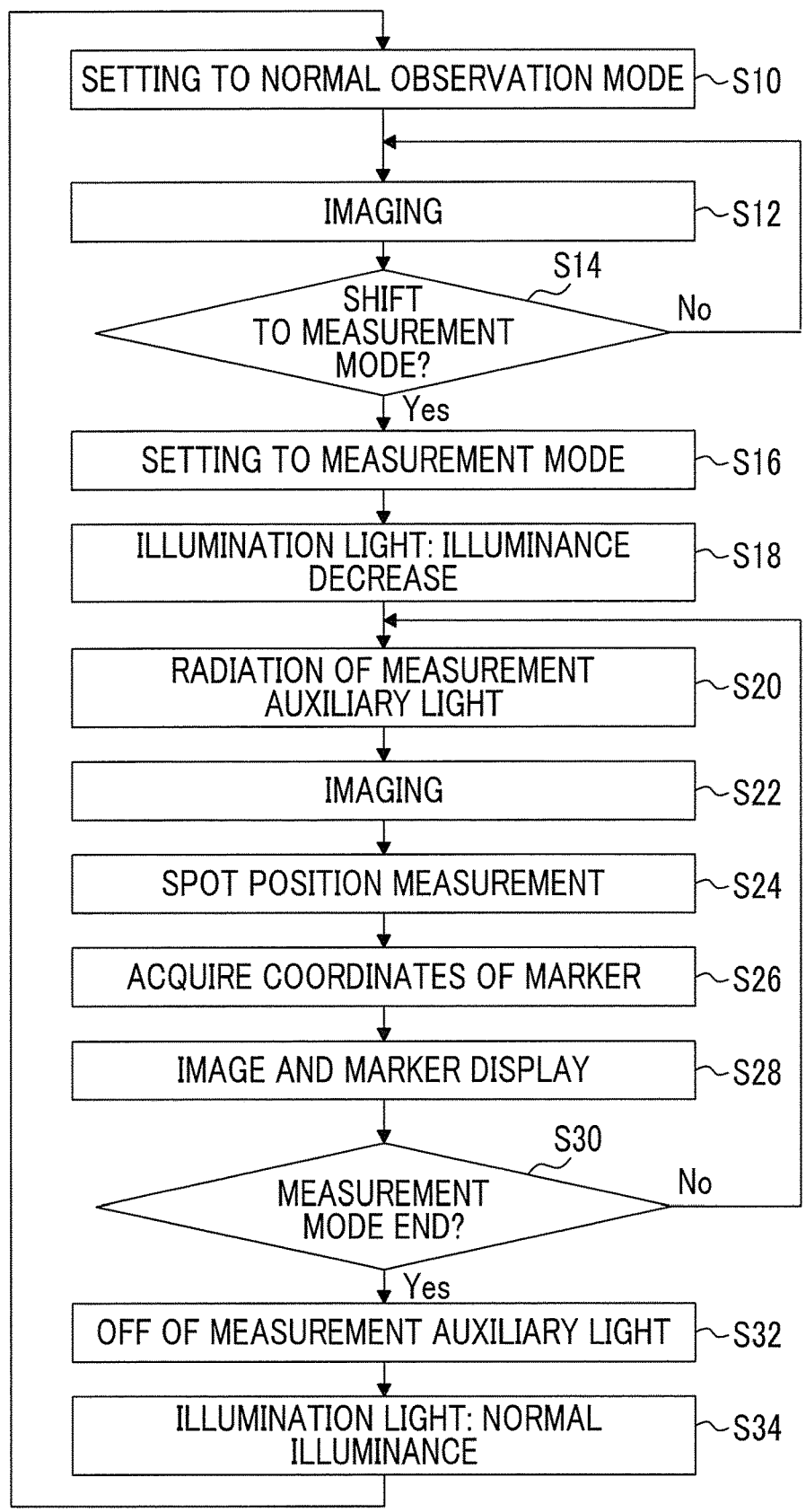
FIG. 8 is a flowchart illustrating the processing of a measurement support method.

Next, the measurement support method for the subject using the endoscope system 10 will be described. FIG. 8 is a flowchart illustrating processing of the measurement support method.

First, the insertion part 104 of the endoscope body 100 is inserted into the subject, and the endoscope system 10 is set to a normal observation mode (Step S10). The normal observation mode is a mode in which the subject is irradiated with the illumination light radiated from the light source device 300 to acquire an image and the subject is observed. The setting to the normal observation mode may be automatically performed by the endoscope processor 200 at the time of the startup of the endoscope system 10 or may be performed in accordance with the operation of the operating part 208 by a user.

In a case where the endoscope system 10 is set to the normal observation mode, the illumination light is radiated to image the subject, and the obtained image is displayed on the monitor 400 (Step S12). As the image of the subject, a still image may be captured or a moving image may be captured. During the imaging, it is preferable to switch the type (the visible light or the infrared light) of the illumination light in accordance with the type of the subject, the purposes of observation, or the like. The user moves the insertion part 104 forward or backward and/or operates to bend the insertion part 104 to direct the distal end hard part 116 to an observation target while viewing an image displayed on the monitor 400 so that the subject to be measured is imaged.

Next, whether or not the normal observation mode shifts to a measurement mode is determined (Step S14). This determination may be performed on the basis of the presence or absence of a user's operation via the operating part 208, or may be performed on the basis of the presence or absence of a switching command from the endoscope processor 200. Additionally, the endoscope processor 200 may alternately set the normal observation mode and the measurement mode at certain fixed frame intervals (such as every one frame or every two frames). In a case where the determination of Step S14 is negative, the process returns to Step S12 and the imaging in the normal observation mode is continued, and in a case where the determination is positive, the process proceeds to Step S16 where switching to the measurement mode is performed.

The measurement mode is a mode in which the laser light (measurement auxiliary light) is radiated from the laser head 506 to form a spot on the subject, and a marker for measuring the size (length) of the subject on the basis of the image of the subject on which the spot is formed is generated and displayed. In the first embodiment, the red laser light is used as the measurement auxiliary light. However, since much of a digestive tract is reddish in an endoscope image, there is a case where the spot is not easily recognized depending on measurement conditions. Thus, in the measurement mode, the illumination light is turned off during the image acquisition and the position measurement of the spot, or the illuminance is lowered to such a degree that the recognition of the spot is not affected (Step S18), and the measurement auxiliary light is radiated from the laser head 506 (Step S20). Such control can be performed by the endoscope processor 200 and the light source control unit 350.

In Step S22, an image of the subject on which the spot is formed with the measurement auxiliary light is captured. In a case where the observation distance is within a measurement range, the spot is formed within the imaging angle of view of the imaging optical system 130. As will be described in detail below, the positions of spots (on the imaging element) within an image are different in accordance with the observation distance, and the sizes (the numbers of pixels) of markers to be displayed are different in accordance with the positions of the spots.

<Changes in Spot Positions According to Observation Distance>

Figure 9:
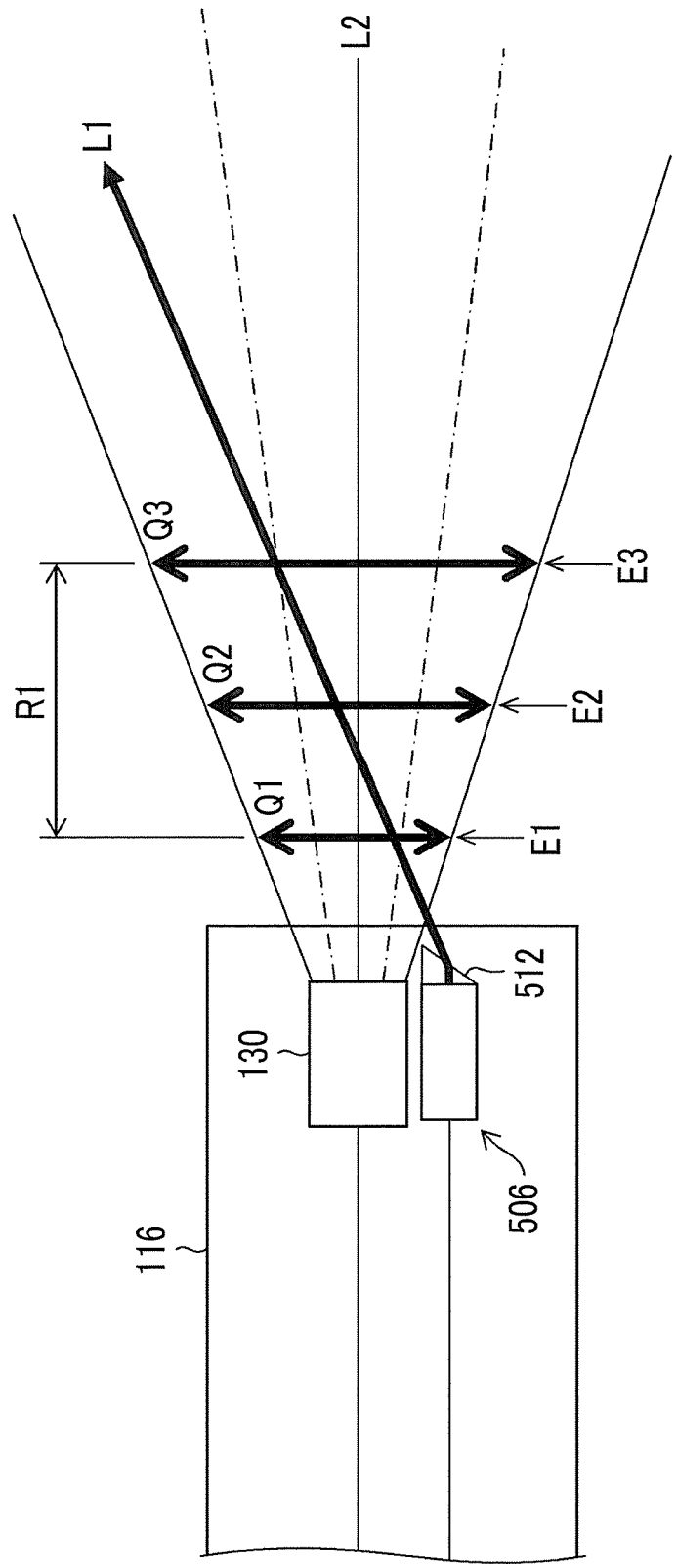
FIG. 9 is a view illustrating a state where the optical axis of the measurement auxiliary light crosses the imaging angle of view of the imaging optical system.

In the first embodiment, in a case where the optical axis L1 of the measurement auxiliary light is projected on the plane including the optical axis L2 of the imaging optical system, the optical axis L1 has the inclination angle, which is not 0 degrees with respect to the optical axis L2, and crosses the angle of view of the imaging optical system 130. Hence, the positions of spots in an image (imaging element) are different depending on distances up to subjects. For example, as illustrated in FIG. 9 (a view illustrating a state where the distal end hard part 116 is seen from a lateral direction within the plane including the optical axis L1 and the optical axis L2), supposing that observation is possible in a range R1 of the observation distance, at a nearest end E1, a distance E2 in the vicinity of the center, and a farthest end E3 in the range R1, it can be understood that the positions of spots in imaging ranges (indicated by arrows Q1, Q2, and Q3) at the respective points (points where the respective arrows and the optical axis L1 intersect each other) are different from each other. In addition, in FIG. 9, the inside of solid lines is the imaging angle of view of the imaging optical system 130, and the inside of one-dot chain lines is a measured angle of view. Measurement is performed at a central portion with a small aberration in the imaging angle of view of the imaging optical system 130. The range R1 and the measurement angle of view in FIG. 9 correspond to a "range where size measurement of a measurement target by a circular marker in the captured image is effective".

Figure 10:
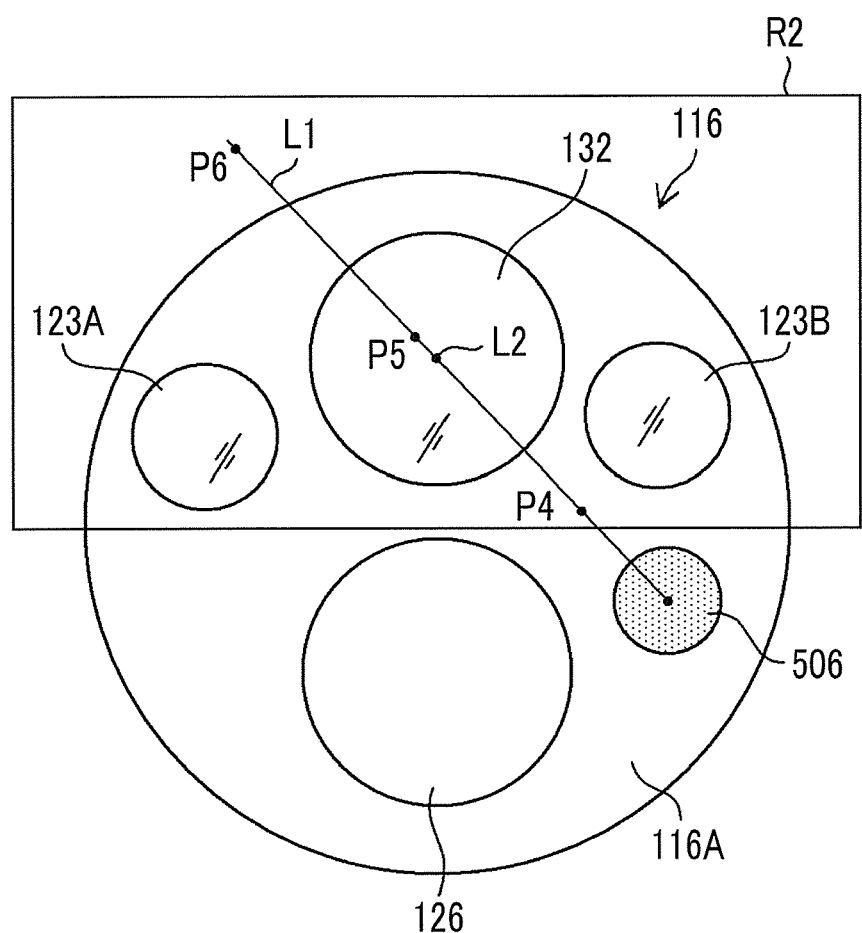
FIG. 10 is a view illustrating a state where spot positions change depending on an imaging distance.

FIG. 10 is a view illustrating a state where the distal end hard part 116 is seen from the front similarly to FIG. 6, and is a view virtually illustrating a relationship between the optical axis L2 of the imaging optical system 130, the optical axis L1 of the measurement auxiliary light, and an imaging range R2 of the imaging element 134. FIG. 10 illustrates a case where the optical axes L1 and L2 are present on the same plane and intersect each other on the plane. In an example of FIG. 10, spot positions P4, P5, and P6 (corresponds to cases where the observation distance is in the vicinity of the nearest end, in the vicinity of the center, and in the vicinity of the farthest end, respectively) according to the observation distance are illustrated.

As illustrated in FIG. 10, it can be understood that the spot position P4 in a case where the observation distance is in the vicinity of the near end and the spot position P6 in a case where the observation distance is in the vicinity of the nearest end are located opposite to each other with respect to the optical axis L2 of the imaging optical system 130. Hence, in the first embodiment, the sensitivity of the movement of the spot positions with respect to the changes in the observation distance is high, and the sizes of subjects can be measured with high accuracy.

In this way, although the spot positions within the captured image (on the imaging element 134) are different in accordance with the relationship between the optical axis L2 of the imaging optical system 130 and the optical axis L1 of the measurement auxiliary light, and the observation distance. However, the number of pixels showing the same actual size (for example, diameter of 5 mm) increases in a case where the observation distance is near, and the number of pixels decreases in a case where the observation distance is far. Hence, as will be described below in detail, coordinates of points indicating a circular marker can be acquired by storing the position (coordinates) of a spot, and coordinates of points indicating an actual size of a measurement target in a subject and indicating the circular marker distorted in accordance with the distortion aberration of the imaging optical system 130 in association with each other, and referring to information stored in accordance with the measured spot positions (coordinates). Since it is not necessary to measure the observation distance itself in a case where the coordinates of the points indicating the circular marker are acquired, the configuration is simple, and the processing load is low.

Figure 11:
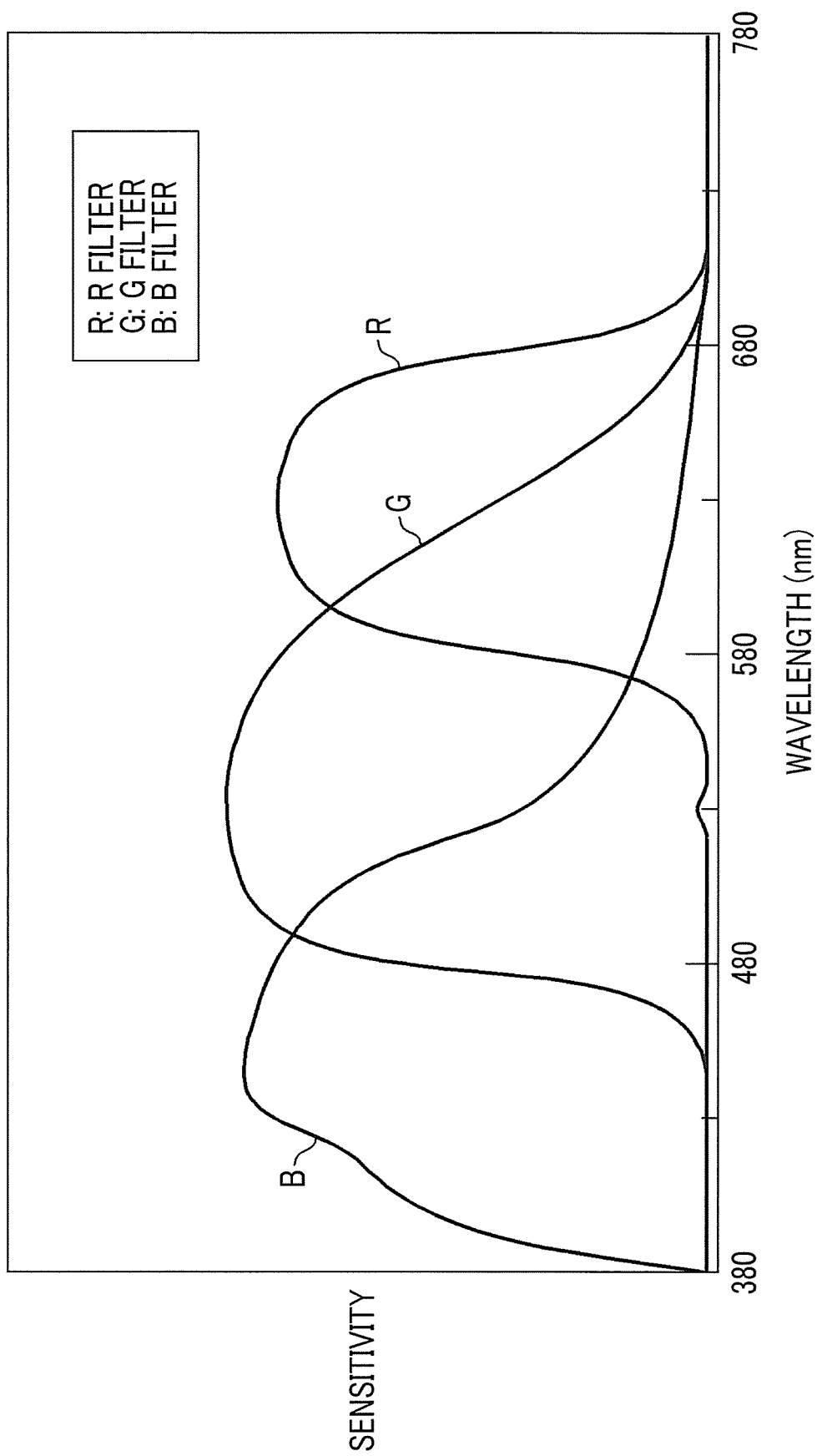
FIG. 11 is a view illustrating a relationship between wavelength and the sensitivity of color filters.

Referring to the flowchart of FIG. 8, the position measurement (Step S24) of a spot on the imaging surface of the imaging element 134 will be described. The position measurement of the spot in Step S24 is performed by an image generated by pixel signals of pixels in which color filters of a filter color of a red (R) color are disposed. Here, a relationship between the wavelength and sensitivity in color filters of respective colors (red, green, and blue) disposed in respective pixels of the imaging element 134 is as illustrated FIG. 11. Additionally, the laser light emitted from the laser head 506 is red laser light with a wavelength of 650 nm. That is, the measurement of the spot positions is performed on the basis of the image generated by the image signals of the pixels (R pixels) in which color filters of a red color with the highest sensitivity with respect to the wavelength of the laser light among color filters of red, green, and blue are disposed. In this case, the position of the spot can be recognized at high speed by providing a threshold value to the signal intensity of R pixels of bit map data or raw image format (RAW) data of the pixel signals to perform binarization and calculating the center of gravity of a white portion (a pixel having a higher signal intensity than the threshold value). In addition, in a case a spot is recognized by an actual image (an image generated by pixel signals of all colors), it is preferable that pixel signals of pixels (G pixels and B pixels) in which green and blue color filters are disposed are provided with threshold values, and pixels in which values of the pixel signals of the G pixels and the B pixels having the bit map data are equal to or smaller than the threshold values are extracted.

In addition, in the measurement mode, as described above, the illumination light is turned off during the image acquisition (Step S22) and the position measurement (Step S24) of the spot, or the illuminance is lowered to such a degree that the recognition of the spot is not affected (Step S18), and the measurement auxiliary light is radiated from the laser head 506 (Step S20). Accordingly, an image with a clear spot can be acquired, the position of the spot can be accurately measured, and a marker of a suitable size can be generated and displayed.

In Step S26, the processor 200 (the CPU 210, the image processing unit 204) acquires the coordinates of the points indicating the actual size of the measurement target in the subject and indicating the circular marker (distorted circular marker) distorted in accordance with the distortion aberration of the imaging optical system 130. As described above, the sizes of markers on the monitor 400 are different in accordance with on the positions of spots within an image (namely, on the imaging surface of the imaging element 134). Thus, coordinates of a spot, and coordinates of points indicating an actual size of a measurement target in a subject and indicating the circular marker distorted in accordance with the distortion aberration of the imaging optical system 130 are stored in association with each other in the memory 212, the processor 200 refers to the memory 212 in accordance with the spot positions measured in Step S24, and the coordinates of the points indicating the distorted circular marker are acquired. A procedure of obtaining a relationship between the spot positions and the coordinates of the points indicating the distorted circular marker will be described below in detail.

Figure 29:
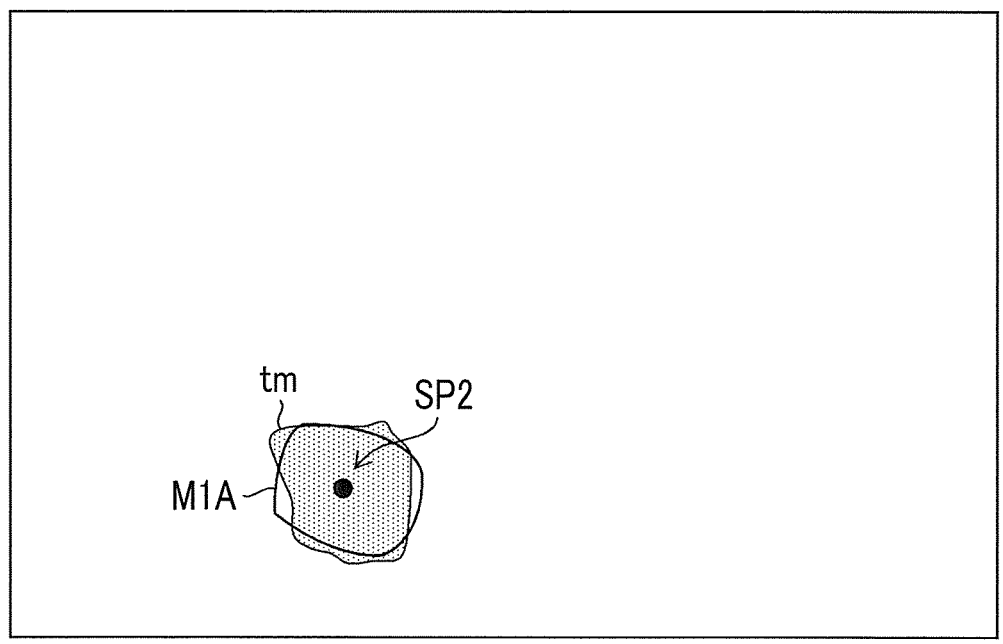
FIG. 29 is a view illustrating a state where the distorted circular marker is overlappingly displayed on a captured image.

In Step S28, the observation image and the distorted circular marker are displayed on the monitor 400 (refer to an example of FIG. 29). In this case, since the distorted circular marker being displayed at a position away from the spot is inaccurate as an indicator, the distorted circular marker is displayed in the vicinity of the spot (with the spot as a center) in the observation image. In addition, in a case where the observation image and the distorted circular marker are displayed, it is not necessary to correct the distortion aberration of the image. For this reason, the appearance of the image not varies due to the correction, and an observer can observe the image without feeling discomfort. Distorted circular markers with different actual sizes (for example, 3 mm, 5 mm, and the like) may be concentrically displayed, and other markers (for example, a cross marker) may be displayed in addition to the distorted circular markers. Additionally, the display conditions (the type, number, actual size, color, and the like of markers) can be set by user's operations via the operating part 208.

In Step S30, whether or not the measurement mode is ended is determined. This determination may be performed on the basis of a user's operation via the operating part 208, or may be performed on the basis of a switching command from the endoscope processor 200. Additionally, similarly to during the shift to the measurement mode, in a case where a certain number of frames have elapsed, the measurement mode may be automatically ended and may return to the normal observation mode. In a case where the determination of Step S30 is negative, the process return to Step S20 and the processing of Step S20 to Step S28 is repeated. In a case where the determination of Step S30 is positive, the process proceeds to Step S32 where the measurement auxiliary light is turned off, subsequently the illuminance of the illumination light is returned to normal illuminance in Step S34, and the process returns to the normal observation mode (returns to Step S10). In addition, in a case where there is no hindrance in the observation in the normal observation mode, the measurement auxiliary light may not be turned off.

As described above, in the endoscope system 10 related to the first embodiment, an accurate indicator (distorted circular marker) can be displayed with a simple configuration, and thereby, the size of the subject can be accurately and easily measured.

<Coordinates of Points Indicating Distorted Circular Marker>

In the first embodiment, coordinates of a spot, and coordinates of points indicating an actual size of a measurement target in a subject and indicating the distorted circular marker in the imaging surface of the imaging element 134 are stored in association with each other in the memory 212, and coordinates are acquired with reference to the memory 212 in accordance with the measured spot positions. Hereinafter, the storage of the coordinates will be described.

<Storage of Marker Coordinates>

In the first embodiment, in a case where the observation distance (imaging distance) has been changed, the coordinates of the points indicating the distorted circular marker are stored with respect to a plurality of points in a trajectory along which the spot moves on the captured image. The movement trajectory of the spot in the captured image in a case where the imaging distance has been changed is determined depending on the relationship between the optical axis L1 of the measurement auxiliary light and the optical axis L2 of the imaging optical system 130, and is a straight line in the case of the relationship illustrated in FIG. 10, but is distorted in accordance with distortion aberration in a case where the distortion aberration is present in the imaging optical system 130.

Figure 12:
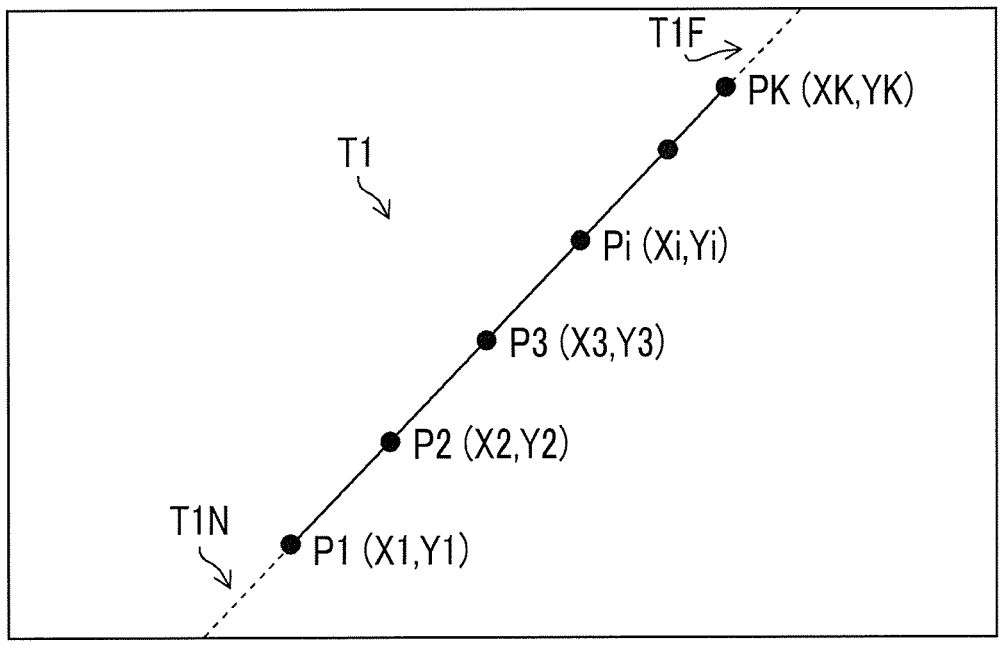
FIG. 12 is a view illustrating a state where coordinates of points indicating a circular marker with respect to a plurality of points in a movement trajectory of a spot are stored.

FIG. 12 is a view illustrating an aspect of the coordinate storage, and illustrates a state where coordinates of points indicating a distorted circular marker are stored for K points (points P1 to PK; K is an integer of 2 or more) in a trajectory T1 of a spot. The point P1 to the point PK are a range (a solid line portion of the trajectory T1; corresponding the inside of the one-dot chain lines in FIG. 9) in which the measurement of size by the distorted circular marker is effective, the point P1 indicates a spot position in a case where the point P1 is a nearest end of an effective measurement range, and the point PK indicates a spot position in a case where the point PK is a farthest end. In addition, the trajectory T1 in FIG. 12 is virtually illustrated.

There are problems such that the distortion aberration becomes large in a case where the spot is present at dotted line portions (peripheral portions of the captured image) of the trajectory T1, a portion of the distorted circular marker is outside the image in a case where the spot is present on the nearest end side (dotted line T1N portion) of the trajectory T1, or the marker becomes small in a case where the spot is present on the farthest end side (dotted line T1F portion), and any of these cases is not suitable for measurement. Thus, in the first embodiment, coordinates are stored in correspondence with the range of the spot position where the size measurement of the measurement target by the distorted circular marker is effective.

Figure 13:
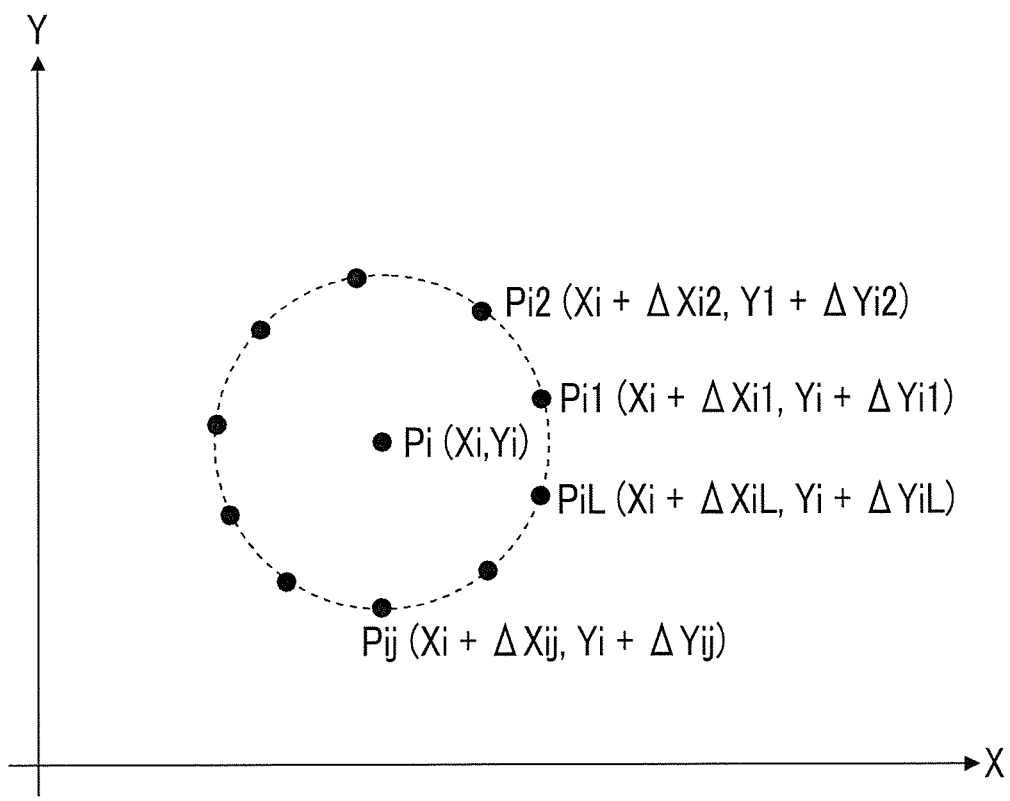
FIG. 13 is a view illustrating a relationship between spot positions and coordinates of points indicating a distorted circular marker.

FIG. 13 is a view illustrating a relationship between spot positions and coordinates of points indicating a distorted circular marker, and illustrates the distorted circular marker with L points (points Pi1, Pi2, . . . , Pij, . . . , PiL; L is an integer) centering on a point Pi (the position of a spot). The value of L can be determined on the basis of the required shape accuracy of the marker, and an accurate marker can be displayed as the number of L is larger. The L points may not be connected to each other by a straight line or a curve. Additionally, FIG. 14 is a view illustrating a state where the spot positions and the coordinates of the points indicating the distorted circular marker are stored in association with each other. Generation of the coordinates (for example, the coordinates of the points Pi1 to PiL with respect to the point Pi) of the points indicating the distorted circular marker will be described below.

<Acquisition of Coordinates>

In a case where the distorted circular marker is displayed, the processor 200 (the CPU 210, the image processing unit 204) acquires the coordinates of the points indicating the distorted circular marker with reference to the memory 212 (storage unit) on the basis of the coordinates of a measured spot. The "acquisition" herein includes using the stored coordinates and using the coordinates generated on the basis of the stored coordinates. Hereinafter, specific aspects of the coordinate acquisition will be described.

<Aspect 1 of Coordinate Acquisition>

Figure 15:
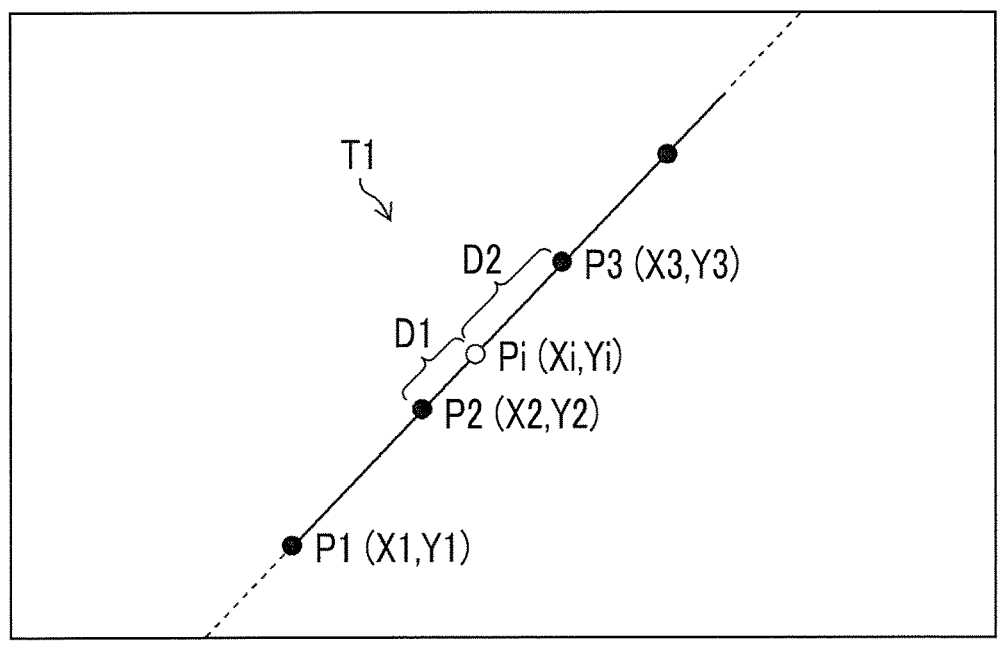
FIG. 15 is a view where coordinates of a marker stored for points of which distances from the spot are equal to or less than a threshold value are acquired.

FIG. 15 is a view illustrating a state where coordinates of points indicating a distorted circular marker are acquired in correspondence with points (K points in the examples of FIGS. 12 to 14), of which distances from a measured spot are equal or smaller than a threshold value, among a plurality of points where coordinates of points indicating the distorted circular marker in the trajectory T1 along which the spot moves are stored. In an example of FIG. 15, a distance between a point P2 and a point Pi where the spot is present is D1, and a distance between a point P3 and the point Pi is D2 (the coordinates of points indicating the distorted circular marker are stored with respect to the points P2 and P3). Additionally, assuming that a threshold value for a distance from the spot is TH, it is assumed that TH<D1 and TH>D2 are established. In this case, in Aspect 1, coordinates (L coordinates in the examples of FIGS. 12 to 14) stored with respect the point P2 of which the distance from the spot is equal to or smaller than the threshold value are acquired as the coordinates indicating the distorted circular marker in the point Pi. In a case where there are a plurality of points of which the distances from the spot are equal to or smaller than the threshold value, it is preferable to acquire coordinates, corresponding to a point of which the distance from the spot is the nearest, to improve the accuracy of the marker. In addition, calculation of the distance from the spot, and comparison with the threshold value can be performed by the processor 200 (the CPU 210, the image processing unit 204). Additionally, the thresholds can be determined in accordance with the accuracy, measurement accuracy, and the like of the distorted circular marker.

<Aspect 2 of Coordinate Acquisition>

Figure 16:
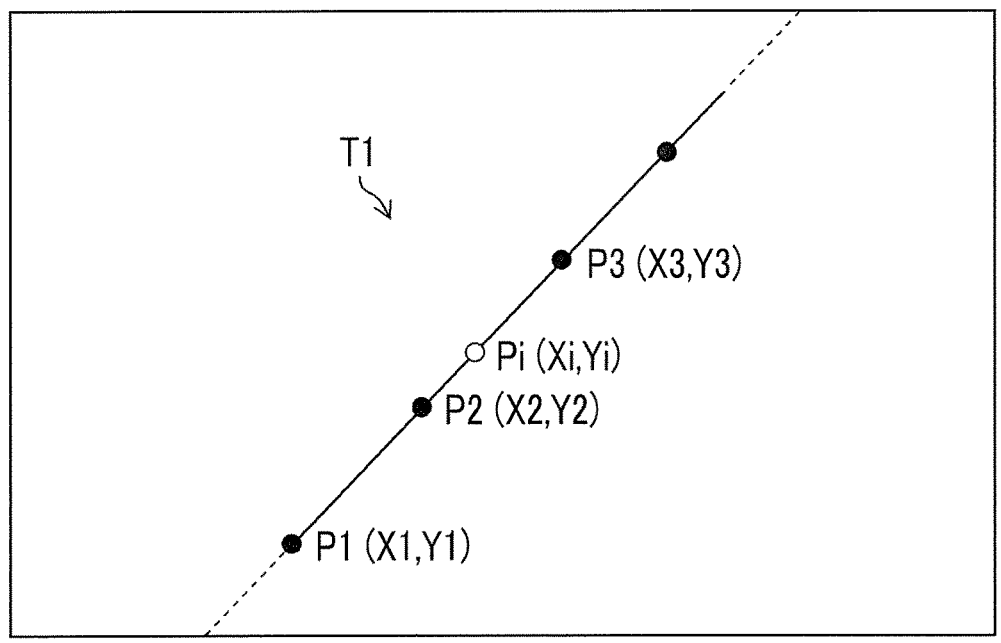
FIG. 16 is a view illustrating a state where coordinates of two points sandwiching a spot position are interpolated, and marker coordinates are acquired.

In Aspect 2, coordinates corresponding to two or more points sandwiching a measured spot among a plurality of points in a trajectory along which a spot moves are interpolated, and coordinates of points indicating a distorted circular marker are acquired. In an example of FIG. 16, coordinates (L coordinates; refer to FIGS. 13 and 14) for the point P2 and coordinates (L coordinates; refer to FIGS. 13 and 14) for the point P3 are interpolated between corresponding points (for example, a point P21 and a point P31 illustrated in FIG. 14), and coordinates of the L points for the point Pi are acquired. Calculation of the interpolation can be performed by the processor 200 (the CPU 210, the image processing unit 204).

<Aspect 3 of Coordinate Acquisition>

Figure 17:
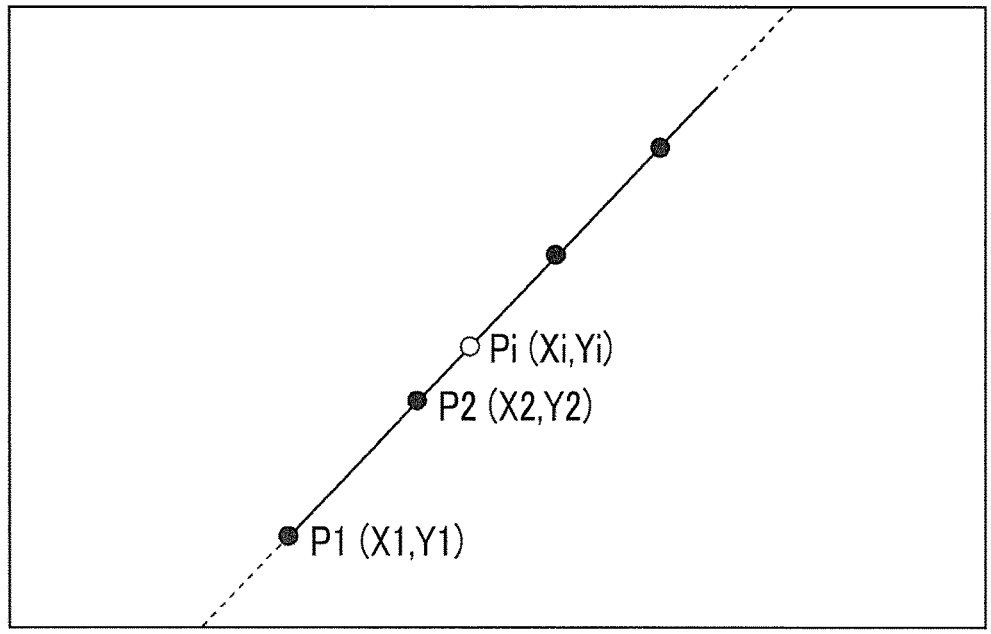
FIG. 17 is a view illustrating a state where coordinates of two points that do not sandwich the spot position are extrapolated, and the marker coordinates are acquired.

In Aspect 3, coordinates corresponding to two or more points that do not sandwich a spot among a plurality of points in a trajectory are extrapolated, and coordinates of points indicating a distorted circular marker are acquired. In an example of FIG. 17, coordinates (L coordinates; refer to FIGS. 13 and 14) for the point P1 and the coordinates (L coordinates; refer to FIGS. 13 and 14) for the point P2 are extrapolated between corresponding points (for example, a point P11 and the point P21 illustrated in FIG. 14), and the coordinates of the L points for the point Pi are acquired. Calculation of the extrapolation can be performed by the processor 200 (the CPU 210, the image processing unit 204).

<Other Aspects>

In the above-described Aspects 1 to 3, coordinates of points indicating a distorted circular marker may be stored for some points on a trajectory. In contrast, coordinates may be stored with respect to all points (pixels) on a trajectory, and the stored coordinates may be acquired as they are. In the case of such aspects, distance calculation, interpolation calculation, and the like between the points can be omitted.

<Coordinate Generation and Storage of Points Indicating Distorted Circular Marker>

Next, specific aspects of the coordinate generation and storage of points indicating a distorted circular marker will be described.

Example 1

<Coordinate Generation and Storage by Interpolation of Actual Measurement Points>

Figure 18:
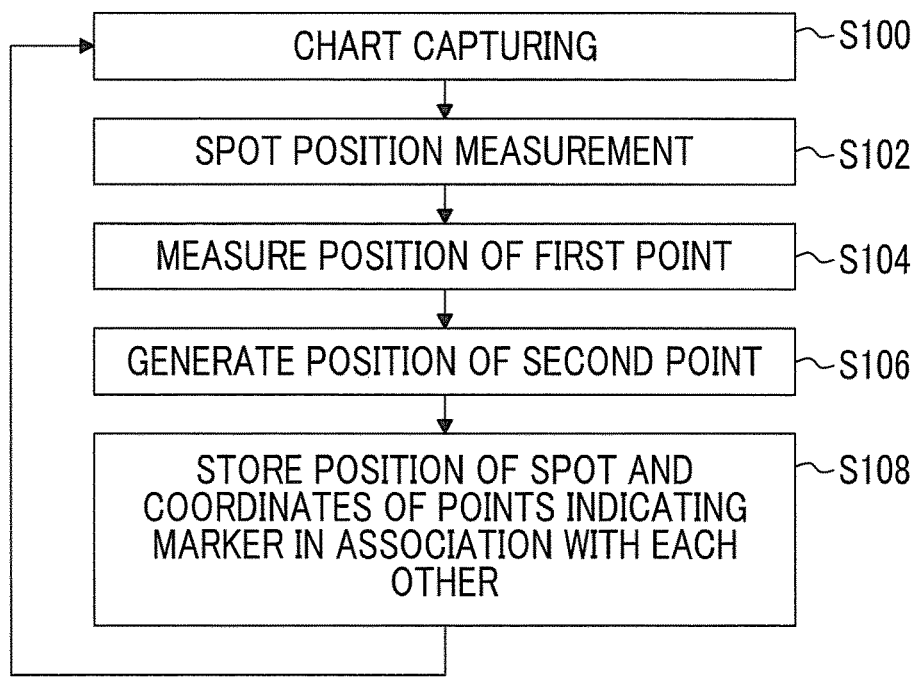
FIG. 18 is a flowchart illustrating processing of Example 1 of coordinate generation and storage.

FIG. 18 is a flowchart illustrating processing of the coordinate generation and storage in Embodiment 1. In Example 1, an actually measured point (first point) and a point (second point) generated by interpolating the actually measured point are stored as coordinates of points indicating a distorted circular marker. Actual measurement, transformation (each processing in the flowchart of FIG. 18), and the like of the coordinates can be performed by the processor 200 (the CPU 210, the image processing unit 204), and the generated coordinates are stored in the memory 212 (storage unit).

First, the measurement auxiliary light is radiated at the imaging distance set in the distance range (refer to the range R1 of FIG. 9) in which measurement by a distorted circular marker is effective with respect to the actual size to be a processing target (although the actual size is described below as 5 mm in diameter, the actual size may have different values in accordance with measurement purposes), and a square lattice-like chart like graph paper is captured (Step S100). In the chart to be captured, it is preferable that the intervals of a lattice are equal to or smaller than the actual size, and the intervals are as fine as possible. Additionally, it is preferable that the intervals of the lattice are intervals (in a case where the actual size of the distorted circular marker has a diameter of 5 mm, the lattice intervals are 0.5 mm, 1 mm, 1.25 mm, 2.5 mm, and the like) of a desired actual size (1/integer). Additionally, by performing imaging in a state where the proximal operating part 102 is operated to change the orientation of the distal end hard part 116 and locate a spot at an intersection point of the lattice, it is preferable to facilitate identification of the first point shown below.

Figure 19:
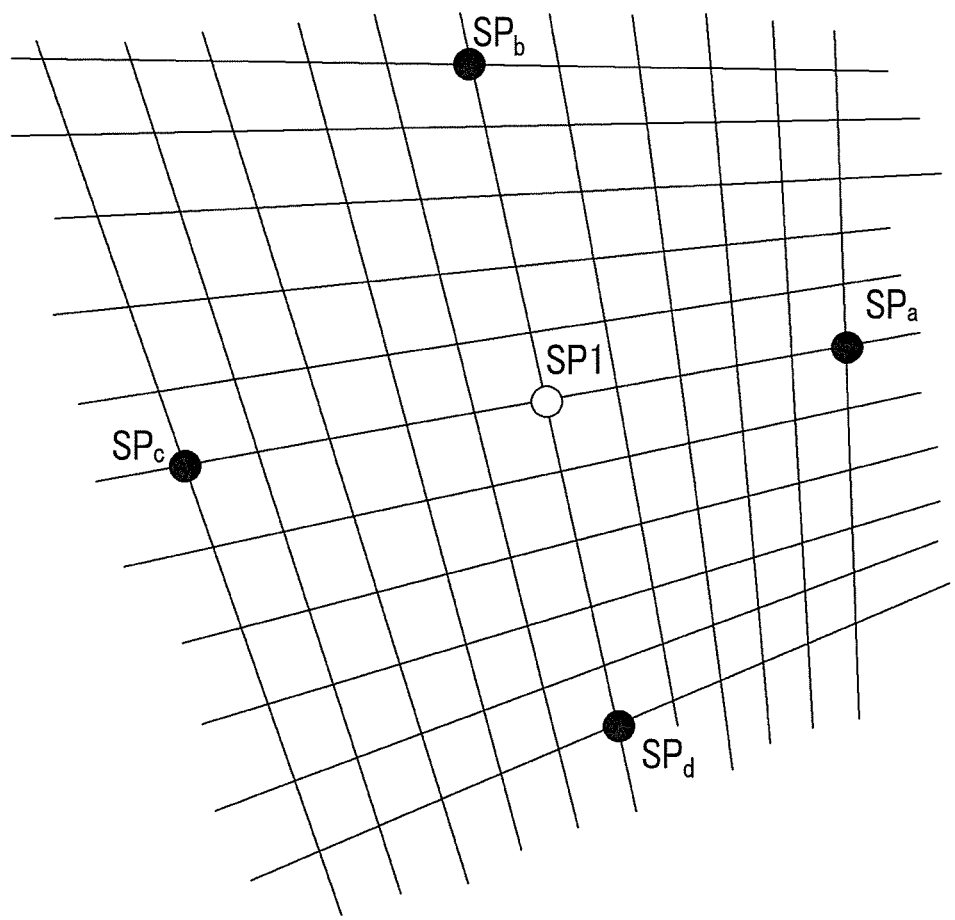
FIG. 19 is a view illustrating a state where the position of a first point is actually measured.

Next, the position of the spot in the captured image is measured (Step S102). FIG. 19 is a view illustrating an example in a case where a square lattice-like chart with intervals of 0.5 mm is captured, and illustrates a spot in which the point SP1 is formed with the laser light (measurement auxiliary light). In the captured image, the square lattice-like chart is distorted depending on the distortion aberration of the imaging optical system 130. In such an image, the position of the spot (the position of the point SP1) is measured (Step S102), and spot position, the position of the first point is measured (actually measured) (Step S104). In an example of FIG. 19, the first point is four points (points SPa, SPb, SPc, and SPd) on a circle centering on the point SP1, and are four points that are present vertically and horizontally on the right of the point SP1 as seen on a square lattice. In the example of FIG. 19, since the actual size has a diameter of 5 mm, and the intervals of the lattice are 0.5 mm, the above-described four points are points separated by five lattice cells vertically and horizontally from the point SP1, and a user can easily identify these four points with the captured image (for example, these four points are clicked with a mouse that the operating part 208 has. The position of the first point can be measured on the basis of this identification result.

Figure 20:
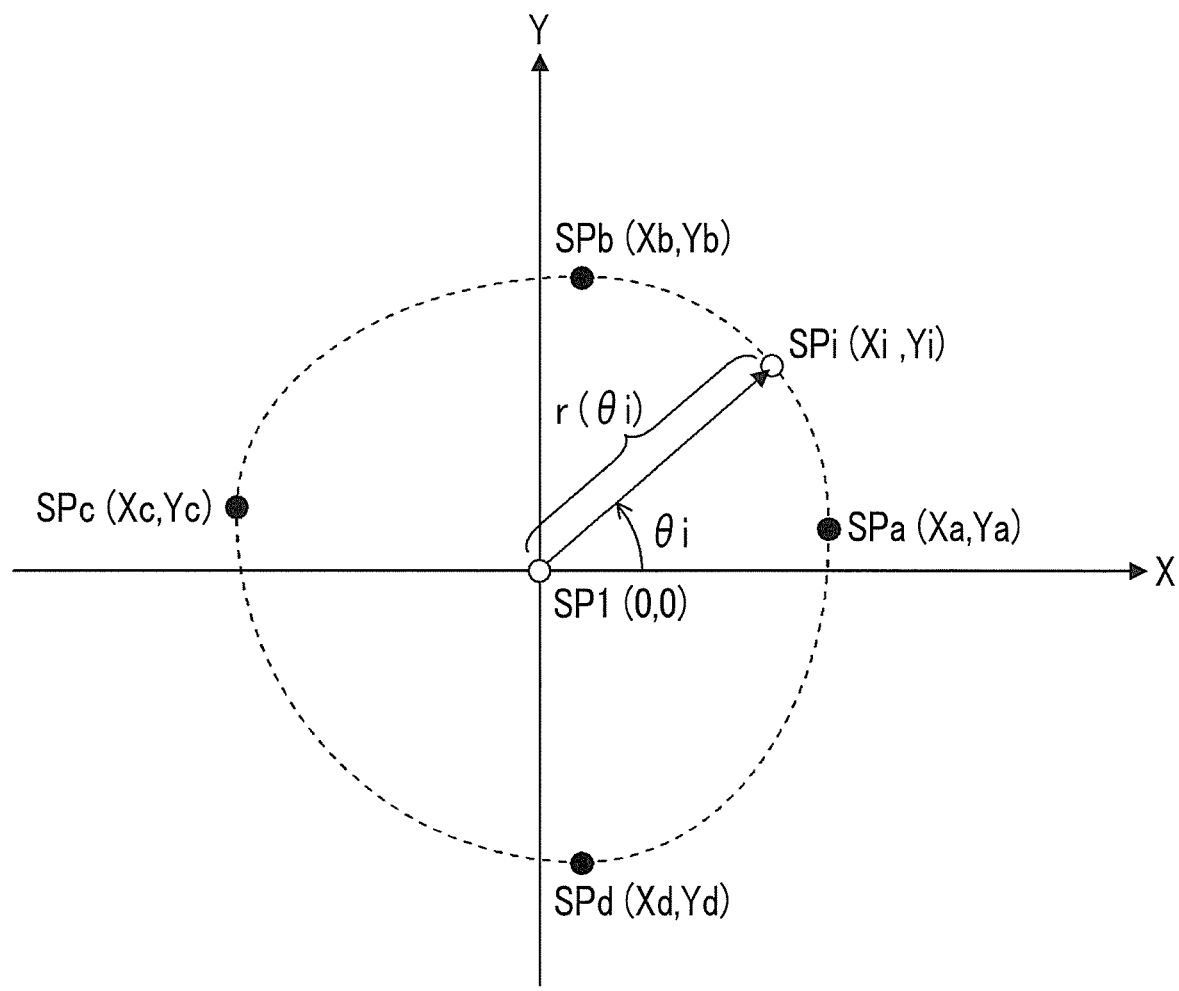
FIG. 20 is a view illustrating a state where the first point is interpolated and a second point is generated.

In a case where the coordinates of the first point are measured, the coordinates of the first point are interpolated, and coordinates of the second point are generated (Step S106). FIG. 20 is a view for illustrating a state where the coordinates of the second point are generated, and relatively displays the first point (the points SPa, SPb, SPc, and SPd) with the point SP1 as a center. The coordinates of the second point can be generated, for example, by linearly interpolating the first point (interpolating 8 and 48) at equal intervals) in an angular direction and a radial direction of a circle. Specifically, between the point SPa and the point SPb, the coordinates (($θi$, $r(θi)$)) in the polar coordinate system and ($Xi$, $Yi$) in the rectangular coordinate system) of the second point (point SPi) can be calculated as follows, using coordinates (($Xa$, $Ya$), ($Xb$, $Yb$)) of these two points. In addition, in the following equation, it is assumed that $(n-1)$ (n is an integer of 2 or more) second points are generated between the points SPa and SPb, and i is an integer of 0 or more and n or less.

$$θa = \arctan(Ya/Xa)$$

$$θb = \arctan(Yb/Xb)$$

$$θi = θa + (θb - θa)/n \times i$$

$$r(θi) = \sqrt{Xa^2 + Ya^2} + (\sqrt{Xb^2 + Yb^2} - \sqrt{Xa^2 + Ya^2})/n \times i$$

$$Xi = r(θi) \times \cos θi$$

$$Yi = r(θi) \times \sin θi \qquad \text{[Equation 1]}$$

Similarly, coordinates of second points can be generated by the interpolation also between the point SPb and the point SPc, between the point SPc and the point SPd, and between the point SPd and the point SPa. In a case where the coordinates of the second points are generated, the coordinates of the first points and the second points as the coordinates of the points indicating the distorted circular marker are associated with the position (the actual position of the point SP1 in the example of FIG. 20) of the spot, and are stored in the memory 212 (Step S108). An aspect of the storage is as illustrated in FIG. 14, and the total number of the first points and the second points is L in this case. In a case where the coordinate acquisition, generation, and storage are completed for the set imaging distance, the process return to Step S100, and the processing is repeated for different imaging distances in the distance range (the range R1 of FIG. 9). Additionally, the actual size may be changed, the above-described processing may be repeated, and coordinates may be stored for a plurality of actual sizes (3 mm, 5 mm, 10 mm, and the like). In this case, distorted circular markers (for example, 3 mm, 5 mm, and the like) with different actual sizes may be concentrically displayed.

Example 2

<Coordinate Generation and Storage by Projective Transformation>

Next, Example 2 of the coordinate generation and storage of the points indicating the distorted circular marker will be described. In Example 2, the coordinates of the circular marker are calculated in the region transformed to the square lattice by projective transformation, the calculated coordinates are inversely transformed, and the coordinates of the distorted circular marker in the distorted lattice region are acquired. Processing, such as generation, transformation (respective kinds of processing in the flowchart of FIG. 21), and the like of the coordinates can be performed by the processor 200 (the CPU 210, the image processing unit 204), and the generated coordinates are stored in the memory 212 (storage unit).

Figure 21:
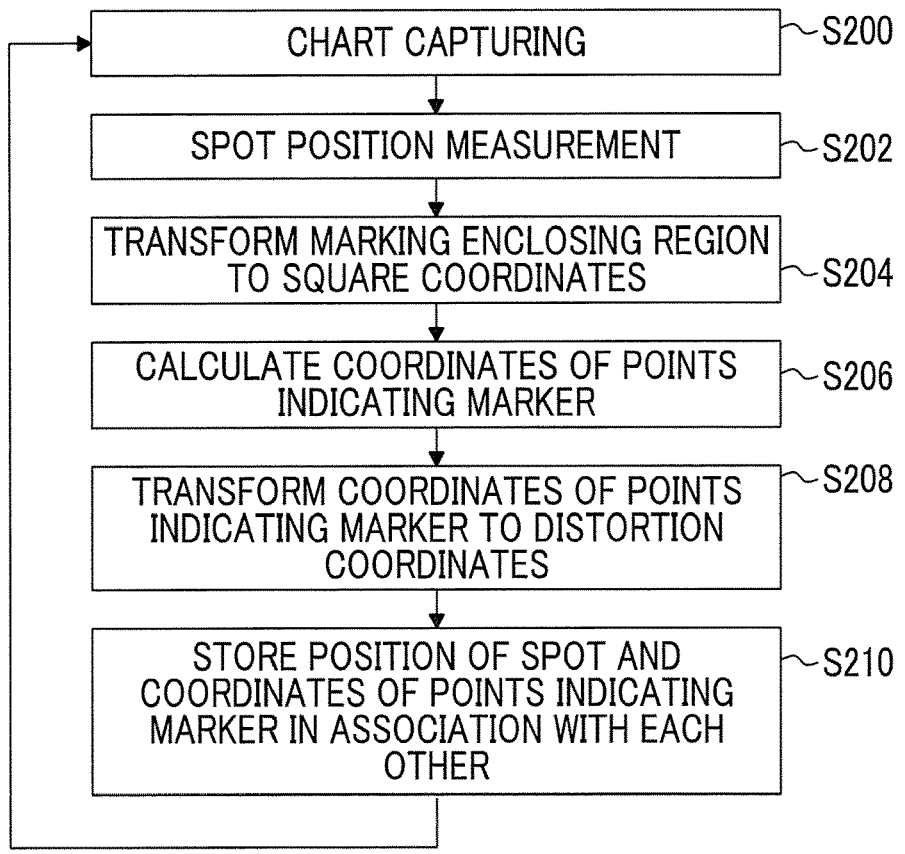
FIG. 21 is a flowchart illustrating the processing of Example 1 of the coordinate generation and storage.
Figure 22:
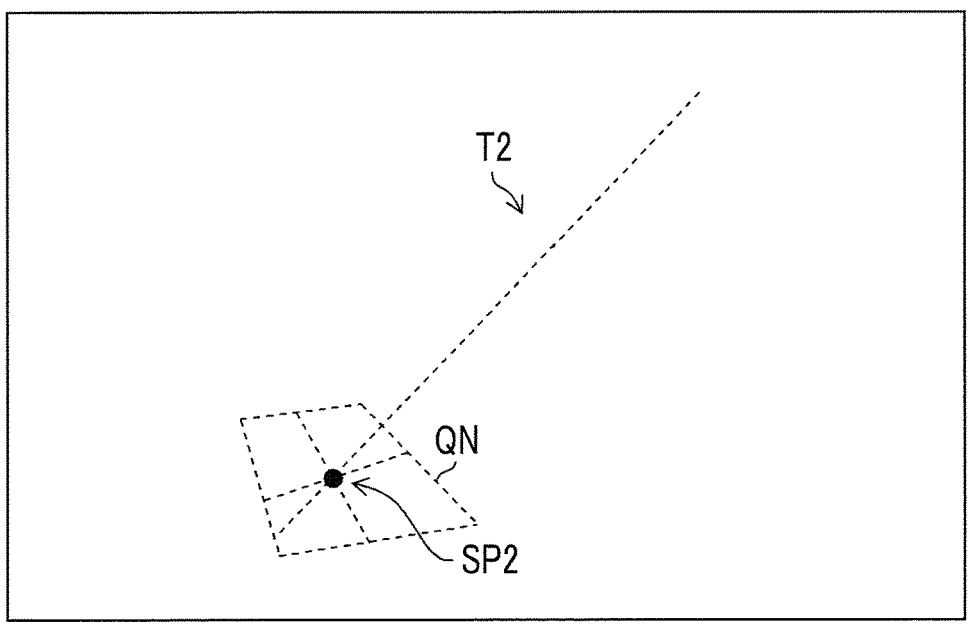
FIG. 22 is a view illustrating a distorted lattice region centering on a spot position.

FIG. 21 is a flowchart illustrating the processing of the coordinate generation and storage in Example 2. First, similarly to Step S100 of Example 1, the measurement auxiliary light is radiated, and a square lattice-like chart is captured (Step S200). It is preferable that a relationship between the chart be imaged and the actual size is the same as that described above for Example 1. After the capturing, the position of a spot is measured (Step S202). FIG. 22 illustrates a distorted lattice region QN that encloses a circular marker centering on the spot (point SP2) in a where the imaging distance is a nearest end (equivalent to the nearest end E1 of FIG. 9) of a measurement distance range (a range of the imaging distance in which measurement can be effectively performed). A trajectory T2 of a spot is an imaginary display. Since the square lattice-like chart is captured, the distorted lattice region QN can be identified on the basis of the position of the spot and the actual size of the marker, similarly to Example 1. In addition, although the distorted lattice region QN is originally the square lattice (square), the distorted lattice region is distorted depending on the distortion aberration of the imaging optical system 130 in the captured image.

<Transformation to Square Lattice Region by Transformation Matrix>

Figure 23:
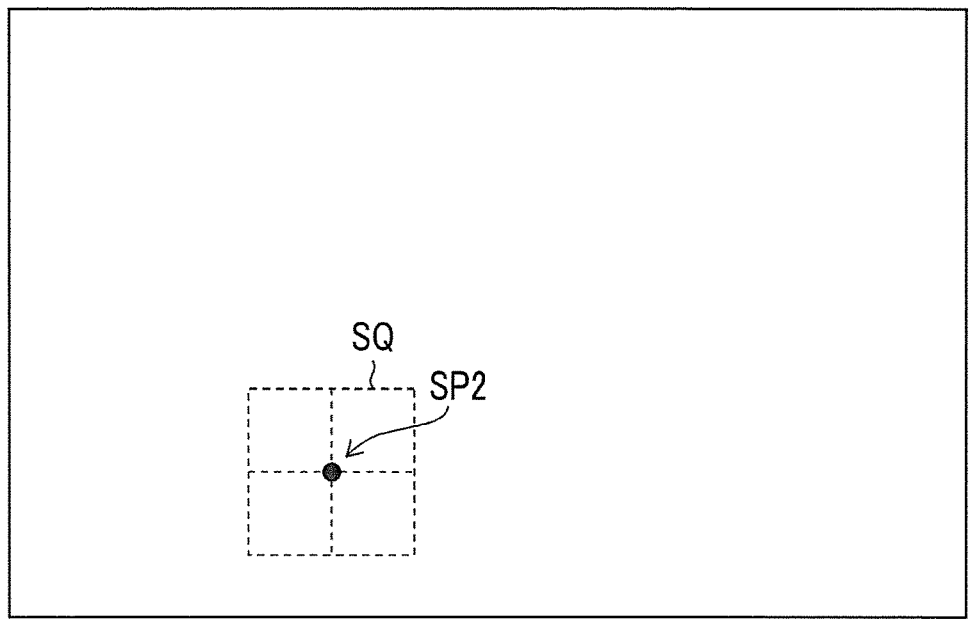
FIG. 23 is a view illustrating a state where the distorted lattice region is converted into a square lattice region.
Figure 24:
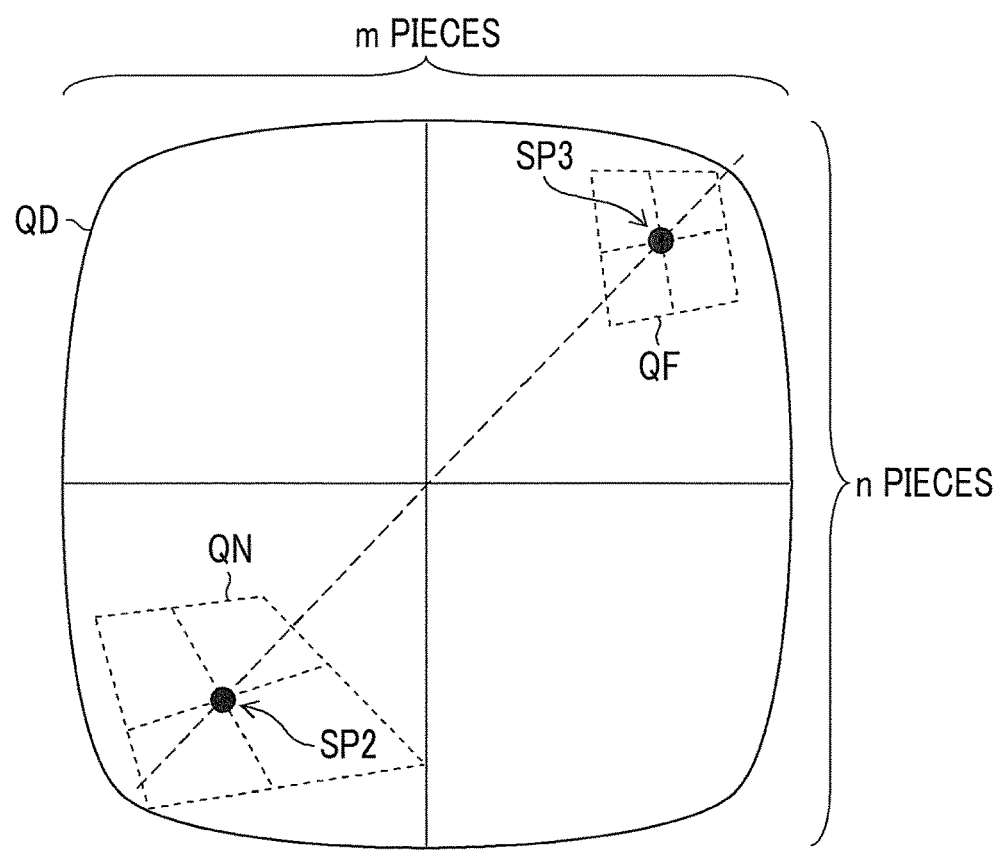
FIG. 24 is a view illustrating a region that stores a transformation matrix and an inverse matrix.

In Step S204, the distorted lattice region (the distorted lattice region QN in the example of FIG. 22 that encloses the marker is transformed to a square lattice region SQ as illustrated in FIG. 23 by affine transformation (one aspect of the projective transformation). Transformation matrices and inverse matrices are obtained by inspection after manufacture of the endoscope system 10. For example, coordinates of lattice points of an image obtained by captured the lattice-like chart are measured, and an affine transformation matrix that transforms the coordinates to square lattice points is obtained. A region where the affine transformation matrix is obtained is a lattice region QD (refer to FIG. 24) that includes the distorted lattice region QN (the spot position is the point SP2) in case the imaging distance is the nearest end of the measurement distance range, and a lattice region QF (the spot position is a point SP3) in a case where the imaging distance is a farthest end, and is provided in a portion of the captured image, and it is not necessary to store transformation matrices for the entire image. In addition, FIG. 24 illustrates an example in a case where the square lattice-like region is distorted to a barrel type depending on the distortion aberration of the imaging optical system 130.

Figure 25:
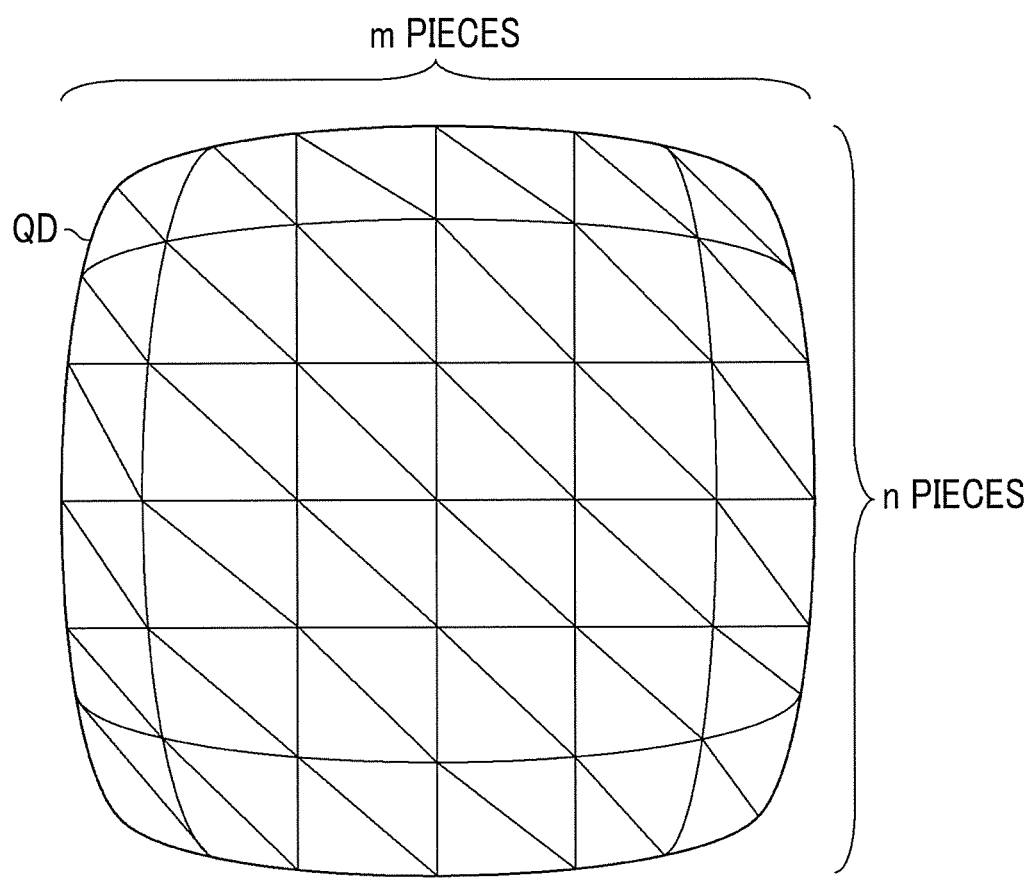
FIG. 25 is a view illustrating division into small regions.
Figure 26:
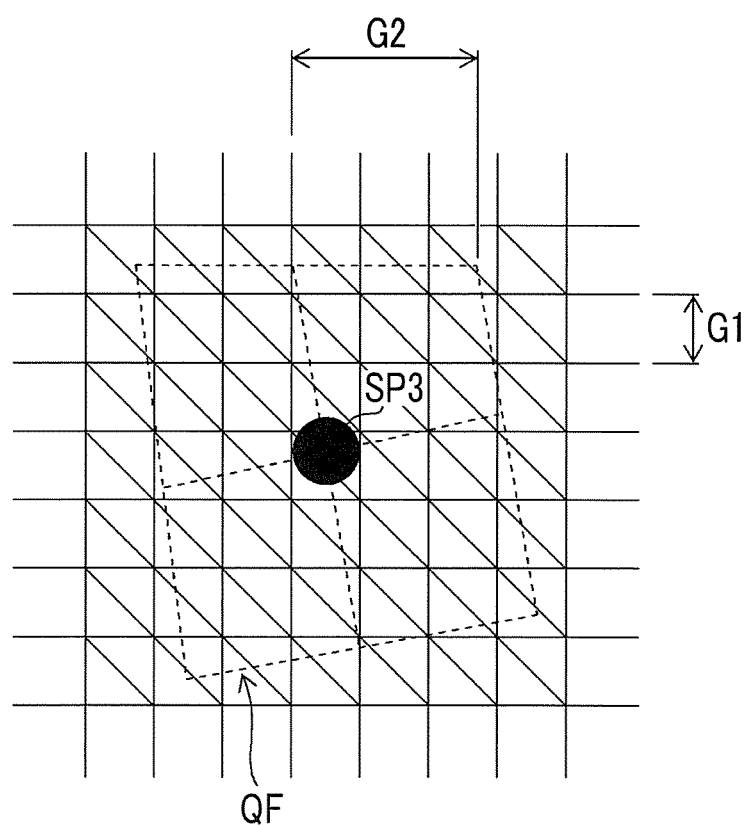
FIG. 26 is a view illustrating a relationship between the size of the small regions and the size of a lattice.

In Example 2, such a lattice region QD is divided into 2×m×n (m, n: integer) small triangular regions (refer to FIG. 25), and affine transformation matrices and their inverse matrices are stored for the split small regions, respectively. The same transformation matrix and its inverse matrix are applied to pixels that belong to the same small region among pixels of the lattice region QD. In addition, as illustrated in FIG. 26 (the vicinity of the lattice region QF in the lattice region QD is enlarged, the division is performed such that "a size G1 of the small regions split into 2×m×n pieces" is smaller than "a size G2 of lattice cells of the lattice region QF in case the imaging distance is the farthest end". By virtue of such division, an accurate distorted circular marker can be displayed also in the farthest end where the display size of the marker becomes small.

In addition, in Example 2, a case where the transformation from the distorted lattice to the square lattice is performed by the affine transformation matrix is described. However, the transformation may be performed by a homography matrix. As described above, the small regions are triangular (constituted of three points) in the affine transformation matrix, whereas the small regions can be quadrangular (constituted of four points). Therefore, the number of small regions can be reduced.

<Coordinate Calculation of Circular Marker>

Figure 27:
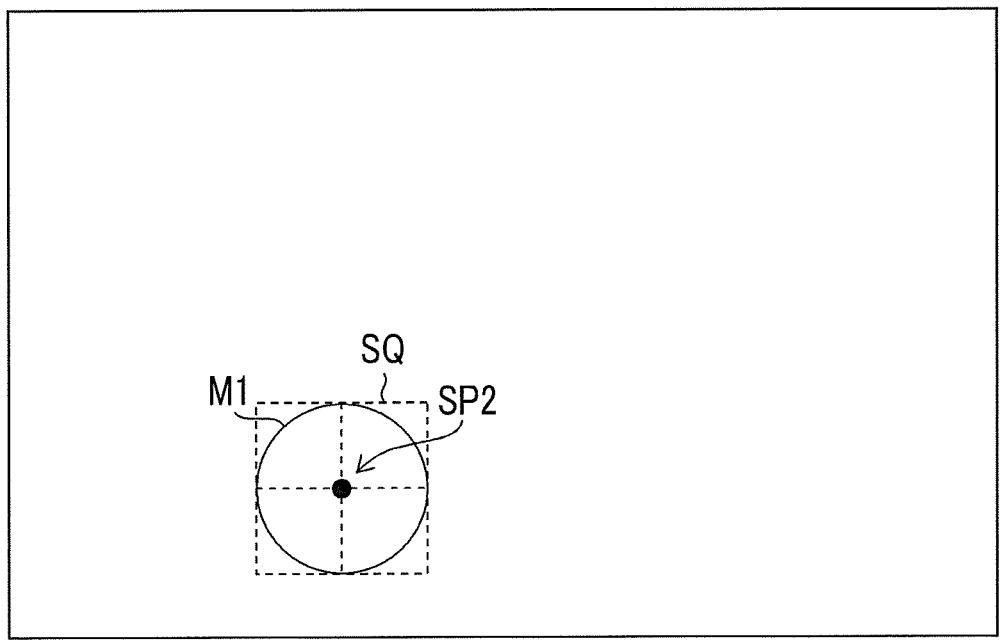
FIG. 27 is a view illustrating a state where the coordinates of a point indicating a circular marker in a square lattice region are calculated.

In a case where the distorted lattice region QN is transformed to the square lattice region SQ by Step S204, coordinates of points indicating a circular marker M1 in the square lattice region SQ are calculated as illustrated in FIG. 27 (Step S206). Since the square lattice region is transformed to the square lattice region, the coordinates of the circular marker can be easily calculated.

<Transformation of Coordinates of Circular Marker to Distortion Coordinates>

Figure 28:
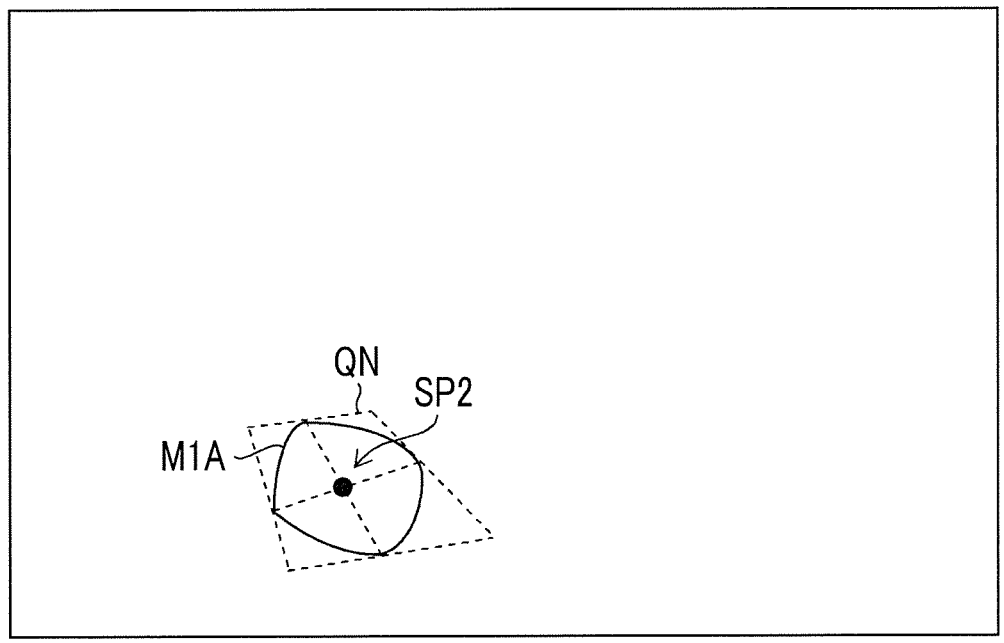
FIG. 28 is a view illustrating a state where the coordinates of a point indicating a circular marker are transformed to a distorted lattice region.

In a case where the coordinates of the circular marker are obtained, the circular marker is transformed to a distorted circular marker M1A, using an inverse matrix of the above-described transformation matrix (Step S208; refer to FIG. 28). The distorted circular marker M1A is displayed to overlap the captured image, as described for the flowchart (Step S28) of FIG. 8. FIG. 29 is an example of display, and illustrates a state where the distorted circular marker M1A centering on the spot (point SP2) formed on a tumor tm is displayed.

In a case where the coordinates of the distorted circular marker M1A are generated, the coordinates are associated with the position (the point SP2 in the example of FIG. 22) of the spot, and are stored in the memory 212 (Step S210). The aspect of the storage is as illustrated in FIG. 14, and the number of points indicating the marker in this case is L. In a case where the acquisition, generation, and storage of the coordinates are completed for the set imaging distance, the process return to Step S200, and the processing is repeated for different imaging distances in the distance range (the range R1 of FIG. 9). Additionally, the actual size may be changed, the above-described processing may be repeated, and coordinates may be stored for a plurality of actual sizes (3 mm, 5 mm, 10 mm, and the like). In this case, distorted circular markers (for example, 3 mm, 5 mm, and the like) with different actual sizes may be concentrically displayed.

<Others>

The measurement support device, the endoscope system, the processor for an endoscope system, the measurement support method in the invention can also be applied to cases where subjects, which are not living bodies, such as a pipe, are measured in addition to measuring the subject that is a living body. Additionally, the measurement support device of the invention can be applied not only to the endoscope but also to cases where the dimensions and shapes of industrial parts are measured.

Although the embodiments and examples of the invention have been described above, it is obvious that the invention is not limited to the above-described aspects, and various modifications can be made without departing from the spirit of the invention.

EXPLANATION OF REFERENCES

10: endoscope system
100: endoscope body
102: proximal operating part
104: insertion part
106: universal cable
108: light guide connector
112: flexible part
114: bending part
116: distal end hard part
116A: distal-end-side end surface
123: illumination unit
123A: illumination lens
123B: illumination lens
126: forceps port
130: imaging optical system
132: imaging lens
134: imaging element
136: driving circuit
138: AFE
170: light guide
200: processor 202: image input controller
204: image processing unit
206: video output unit
208: operating part
210: CPU
212: memory
300: light source device
310: light source
310A: visible light source
310B: infrared light source
330: stop
340: condensing lens
350: light source control unit
400: monitor
500: laser module
501: fiber covering
502: laser light source module
503: condensing lens
504: optical fiber
506: laser head
507: reinforcing material
508: ferrule
509: housing
510: GRIN lens
512: prism
AL1: apex angle
E1: nearest end
E2: distance
E3: farthest end
IA: imaging range
L1: optical axis
L2: optical axis
M1: circular marker
M1A: distorted circular marker
P1: point
P2: point
P3: point
Pi: point
Pi1: point
Pi2: point
Pij: point
PiL: point
PK: point
P4: spot positions
P5: spot positions
P6: spot positions
Q1: arrow
Q2: arrow
Q3: arrow
QD: lattice region
QF: lattice region
QN: distorted lattice region
R1: range
R2: imaging range
S10 to S210: respective steps of measurement support method
SQ: square lattice region
T1: trajectory
T2: trajectory
tm: tumor

What is claimed is:

1. A measurement support device comprising:
a head that emits measurement auxiliary light;
an imaging unit that captures an image of a subject on which a spot is formed with the measurement auxiliary light via an imaging optical system and an imaging element;
a measurement unit that measures coordinates of the spot in the image;
a storage unit that stores the coordinates of the spot and coordinates of points indicating an actual size of a measurement target in the subject and indicating a circular marker distorted in accordance with distortion aberration of the imaging optical system in association with each other and that stores the coordinates of the points indicating the circular marker with respect to a plurality of points in a trajectory along which the spot moves on the image in a case where an imaging distance of the image is changed;
a coordinate acquisition unit that refers the storage unit on the basis of the measured coordinates of the spot and acquires the coordinates of the points indicating the circular marker corresponding to the coordinates of the spot; and
a display control unit that causes the circular marker to be displayed in the vicinity of the spot in the image on the basis of the acquired coordinates,
wherein the head emits the measurement auxiliary light that has an inclination angle that is not 0 degrees with respect to an optical axis of the imaging optical system and crosses an angle of view of the imaging optical system, in a case where an optical axis of the measurement auxiliary light is projected on a plane including the optical axis of the imaging optical system.

2. The measurement support device according to claim 1, wherein the coordinate acquisition unit acquires the coordinates of the points indicating the circular marker corresponding to a point of which a distance from the spot is equal to or smaller than a threshold value, among the plurality of points.

3. The measurement support device according to claim 1, wherein the coordinate acquisition unit acquires the coordinates of the points indicating the circular marker by interpolating coordinates corresponding to two or more points sandwiching the spot, among the plurality of points.

4. The measurement support device according to claim 1, wherein the coordinate acquisition unit acquires the coordinates of the points indicating the circular marker by extrapolating coordinates corresponding to two or more points that do not sandwich the spot, among the plurality of points.

5. The measurement support device according to claim 1, wherein the storage unit stores the coordinates of the points indicating the circular marker in correspondence with a range where size measurement of the measurement target by the circular marker is effective, in the image.

6. The measurement support device according to claim 1, wherein the storage unit stores coordinates of a plurality of first points, which are actually measured in correspondence with a circle centering on the spot, and coordinates of a plurality of second points generated by interpolating the plurality of first points as the coordinates of the points indicating the circular marker, and
wherein the coordinate acquisition unit acquire the coordinates of the plurality of first points and the coordinates of the plurality of second points as the coordinates of the points indicating the circular marker.

7. The measurement support device according to claim 6, wherein the storage unit stores coordinates of points, which are obtained by linearly interpolating the plurality of first points in an angular direction and a radial direction of the circle, as the coordinates of the plurality of second points.

8. The measurement support device according to claim 1, wherein the storage unit stores a transformation matrix for projectively transform a distorted lattice region including the circular marker centering on the spot to a square lattice region, in the image, and wherein the coordinate acquisition unit acquires the coordinates of the points indicating the circular marker in the square lattice region transformed by the transformation matrix, and acquires the coordinates of the points indicating the circular marker in the distorted lattice region by inversely transforming the acquired coordinates by an inverse matrix of the transformation matrix.

9. The measurement support device according to claim 8, wherein the storage unit stores the transformation matrix for each of a plurality of small regions obtained by dividing the distorted lattice region and the square lattice region into 2×m×n pieces in a case where m and n are positive integers, and wherein the coordinate acquisition unit applies a same transformation matrix out of the plurality of transformation matrices and a same inverse matrix out of the plurality inverse matrices to pixels, which belong to a same small region, among pixels of the image.

10. The measurement support device according to claim 9, wherein the storage unit stores the transformation matrices, using a plurality of regions, which include the distorted lattice region in a case where the imaging distance is a farthest end of a measurement distance range, and the distorted lattice region in a case where the imaging distance is a nearest end of the measurement distance range, and are obtained by dividing a partial region in the image, and which are divided to be smaller than a size of lattice cells of the distorted lattice region in the farthest end, as the plurality of small regions, and wherein the coordinate acquisition unit acquires the coordinates of the points indicating the circular marker, using the transformation matrices stored for the plurality of small regions.

11. The measurement support device according to claim 8, wherein the transformation matrix is an affine transformation matrix.

12. An endoscope system comprising:
the measurement support device according to claim 1.

13. The endoscope system according to claim 12, further comprising:
an endoscope having an insertion part to be inserted into a subject, the insertion part having a distal end hard part and a bending part connected to a proximal end side of the distal end hard part, and a flexible part connected to a proximal end side of the bending part, and an operating part connected to a proximal end side of the insertion part,
wherein the distal end hard part is provided with the head, and an imaging lens for forming an optical image of the spot on the imaging element.

14. A processor for the endoscope system according to claim 12, the processor comprising the measurement unit, the storage unit, the coordinate acquisition unit, and the display control unit.

* * * * *